US009410267B2

(12) United States Patent
Parker et al.

(10) Patent No.: US 9,410,267 B2
(45) Date of Patent: Aug. 9, 2016

(54) METHODS AND DEVICES FOR THE FABRICATION OF 3D POLYMERIC FIBERS

(75) Inventors: Kevin Kit Parker, Waltham, MA (US); Mohammad Reza Badrossamay, Somerville, MA (US); Josue Adrian Goss, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/320,031

(22) PCT Filed: May 13, 2010

(86) PCT No.: PCT/US2010/034662
§ 371 (c)(1),
(2), (4) Date: Jan. 30, 2012

(87) PCT Pub. No.: WO2010/132636
PCT Pub. Date: Nov. 18, 2010

(65) Prior Publication Data
US 2012/0135448 A1    May 31, 2012

Related U.S. Application Data

(60) Provisional application No. 61/177,894, filed on May 13, 2009.

(51) Int. Cl.
*D01D 5/18*    (2006.01)
*C12N 5/00*    (2006.01)
(Continued)

(52) U.S. Cl.
CPC ............... *D01D 5/18* (2013.01); *C12N 5/0068* (2013.01); *C12N 5/0075* (2013.01); *C12N 5/0657* (2013.01); *G01N 33/5082* (2013.01); *G01N 33/5088* (2013.01); *C12N 2533/30* (2013.01); *C12N 2533/40* (2013.01)

(58) Field of Classification Search
CPC ........................................................ D01D 5/18
USPC ........................................................ 425/8, 9
See application file for complete search history.

(56) References Cited

U.S. PATENT DOCUMENTS 2,067,410 A * 1/1937 Newnham ................. 416/220 R
2,336,743 A * 12/1943 Manning ........................ 156/74
(Continued)

FOREIGN PATENT DOCUMENTS

WO    WO 03/099230    12/2003
WO    WO 2004/032713    4/2004
(Continued)

OTHER PUBLICATIONS

Harfenist, S., et al., Direct Drawing of Suspended Filamentary Micro- and Nanostructures from Liquid Polymers. Nano Letters, 2004;4(10):1931-1937.
(Continued)

*Primary Examiner* — Yogendra Gupta
*Assistant Examiner* — Joseph Leyson
(74) *Attorney, Agent, or Firm* — McCarter & English, LLP; Deborah L. Nagle; Anita M. Bowles

(57) ABSTRACT

The present invention provides methods and devices for the fabrication of 3D polymeric fibers having micron, sub-micron, and nanometer dimensions, as well as methods of use of these polymeric fibers.

20 Claims, 16 Drawing Sheets

(51) Int. Cl.
*C12N 5/077* (2010.01)
*G01N 33/50* (2006.01)

(56) References Cited

U.S. PATENT DOCUMENTS

| | | | |
|---|---|---|---|
| 4,345,355 | A | 8/1982 | Berchoux et al. |
| 5,066,430 | A * | 11/1991 | Matthews ................ 264/8 |
| 5,441,754 | A * | 8/1995 | Evans, Sr. .............. 426/465 |
| 5,494,616 | A * | 2/1996 | Voelker et al. .............. 264/8 |
| 6,596,048 | B1 * | 7/2003 | Tuffal et al. ............... 55/527 |
| 2002/0182241 | A1 | 12/2002 | Borenstein et al. |
| 2003/0147983 | A1 | 8/2003 | Berrigan et al. |
| 2004/0037813 | A1 | 2/2004 | Simpson et al. |
| 2005/0136253 | A1 * | 6/2005 | Michael et al. ............ 428/364 |
| 2006/0060999 | A1 | 3/2006 | Amagasa et al. |
| 2006/0105275 | A1 | 5/2006 | Maloney et al. |
| 2007/0207186 | A1 | 9/2007 | Scanlon et al. |
| 2008/0023888 | A1 | 1/2008 | Brang et al. |
| 2008/0136054 | A1 * | 6/2008 | Fabbricante et al. ...... 264/211.1 |
| 2008/0211121 | A1 * | 9/2008 | Lai et al. ................... 264/8 |
| 2008/0237934 | A1 | 10/2008 | Reneker et al. |
| 2008/0242171 | A1 | 10/2008 | Huang et al. |
| 2009/0232874 | A1 | 9/2009 | Chu et al. |
| 2009/0232920 | A1 | 9/2009 | Lozano et al. |
| 2009/0269429 | A1 | 10/2009 | Lozano et al. |
| 2009/0280207 | A1 | 11/2009 | Lozano et al. |
| 2009/0280325 | A1 | 11/2009 | Lozano et al. |
| 2010/0028999 | A1 | 2/2010 | Nain |
| 2010/0037576 | A1 | 2/2010 | Claasen et al. |

FOREIGN PATENT DOCUMENTS

| | | |
|---|---|---|
| WO | WO 2005/017226 | 2/2005 |
| WO | WO 2012/068402 | 5/2012 |

OTHER PUBLICATIONS

Li, D. and Xia, Y. Electrospinning of nanofibers: Reinventing the wheel? Advanced Materials 2004;16(14):1151-1170.

Feinberg, A.W., et al. Muscular Thin Films for Building Actuators and Powering Devices. Science 2007; 317(5843):1366-1370.

Arumuganathar, S. and Jayasinghe, S.N. Living Scaffolds (Specialized and Unspecialized) for Regenerative and Therapeutic Medicine. Biomacromolecules 2008; 9(3):759-766.

Weitz R.T., et al. Polymer Nanofibers via Nozzle-Free Centrifugal Spinning. Nano Letters 2008;8(4)1187-1191.

Xie, J., et al. Putting Electrospun Nanofibers to Work for Biomedical Research. Macromolecular Rapid Communications 2008;29(22): 1775-1792.

Madurantakam, P.A., et al. Science of nanofibrous scaffold fabrication: strategies for next generation tissue-engineering scaffolds. Nanomedicine 2009;4(2):193-206.

Madurantakam, P.A., et al. Multiple factor interactions in biomimetic mineralization of electrospun scaffolds. Biomaterials 2009; 30(29):5456-5464.

Nisbet D.R., et al. Review paper: a review of the cellular response on electrospun nanofibers for tissue engineering. J Biomater Appl. Jul. 2009;24(1):7-29.

Pabba, S., et al. Biopolymerization-driven self-assembly of nanofiber air-bridges. Soft Matter 2009;5(7):1378-1385.

Alford P.W., et al. Biohybrid thin films for measuring contractility in engineered cardiovascular muscle. Biomaterials. 2010;31(13):3613-3621.

Badrossamay, M.R. et al. Nanofiber assembly by rotary jet-spinning. Nano Letters 2010;10(6):2257-2261.

International Search Report and Written Opinion in PCT/US11/61241, mailed Apr. 11, 2012.

* cited by examiner

METHODS AND DEVICES FOR THE FABRICATION OF 3D POLYMERIC FIBERS

RELATED APPLICATIONS

This application claims priority to U.S. Provisional Application No. 61/177,894, filed on May 13, 2009, the entire contents of which are incorporated herein by this reference.

GOVERNMENT SUPPORT

This invention was supported, in whole or in part, by Harvard University Nanoscale Science and Engineering Center (NSEC), Harvard Materials Research Science and Engineering Center (MRSEC), both sponsored by the National Science Foundation Harvard Center for Nanoscale Systems (CNS), Wyss Institute for Biologically-Inspired Engineering, the National Institutes of Health ( NIH R01 HL079126-01A2), and the National Science Foundation (PHY-0646094). The United States Government has certain rights in the invention.

BACKGROUND OF THE INVENTION

Polymeric fibers, such as nanofibers, have a broad array of uses including use as catalytic substrates, photonics, filtration, protective clothing, cell scaffolding, drug delivery and wound healing. Structures prepared using nanofibers are the best candidates for tissue engineering for, e.g., orthopedic, muscular, vascular and neural prostheses, and regenerative medicine due to their high surface to mass ratio, high porosity for, e.g., breathability, encapsulation of active substances, and fiber alignment, and because they can be easily wound into different shapes (Madurantakam, et al. (2009) *Nanomedicine* 4:193-206; Madurantakam, P. A., et al. (2009) *Biomaterials* 30(29):5456-5464; Xie, et al. (2008) *Macromolecular Rapid Communications* 29:1775-1792).

The most common process for fabricating nanofibers is electrospinning. Briefly, electrospinning is a process that uses high voltage to create an electric field between a droplet of polymer solution at the tip of a needle and a collector plate. One electrode of the voltage source is placed into the solution and the other is connected to the collector. This creates an electrostatic force. As the voltage is increased, the electric field intensifies causing a force to build up on the pendant drop of polymer solution at the tip of the needle. This force acts in a direction opposing the surface tension of the drop. The increasing electrostatic force causes the drop to elongate forming a conical shape known as a Taylor cone. When the electrostatic force overcomes the surface tension of the drop, a charged, continuous jet of solution is ejected from the cone. The jet of solution accelerates towards the collector, whipping and bending wildly. As the solution moves away from the needle and toward the collector, the jet rapidly thins and dries as the solvent evaporates. On the surface of the grounded collector, a nonwoven mat of randomly oriented solid nanofibers is deposited (Zufan (2005) *Final RET Report*; Xie, J. W. et al. (2008) *Macromolecular Rapid Communications* 29(22):1775-1792; Reneker, D. H., et al. (2007) *Advances in Applied Mechanics* 41:43-195; Dzenis, Y. (2004) *Science* 304(5679):1917-1919; Rutledge, G. C. and Yu, J. H. (2007) "Electrospinning" In *Encyclopedia of Polymer Science and Technology*, John Wiley & Sons: New Jersey; Krogman, K. C., et al. (2009) *Nature Materials* 8(6):512-518; Pham, Q. P., et al. (2006) *Tissue Engineering* 12(5):1197-1211; Boland, E. D., et al. (2001) *Journal of Macromolecular Science-Pure and Applied Chemistry* 38(12):1231-1243; Teo, W. E. and Ramakrishna, S. (2006) *Nanotechnology* 17(14):R89-R106; Li, D.; Xia, Y. N. (2004) *Advanced Materials* 16(14):1151-1170; Greiner, A. and Wendorff, J. H. (2007) *Angewandte Chemie-International Edition* 46(30):5670-5703).

However there are multiple drawbacks associated with electrospinning, such as the requirement for a high voltage electrical field, low production rate, the requirement for precise solution conductivity, and the need for additional devices for producing aligned fiber structures (Lia and Xia (2004) *Advanced Materials* 16:1151-1170; Weitz, et al. (2008) *Nano Letters* 8:1187-1191; Arumuganathar, S, and Jayasinghe, S, N. (2008) *Biomacromolecules* 9(3):759-766).

Accordingly, there is a need in the art for improved methods and devices for the fabrication of polymeric fibers, such as nanofibers.

SUMMARY OF THE INVENTION

Described herein are improved methods and devices for the fabrication of polymeric fibers having micron, submicron, and nanometer dimensions. The polymeric fibers produced according to the methods disclosed herein can be, for example, used as extracellular matrix and, together with cells, may also be used in forming engineered tissue. The polymeric fibers of the invention may also be combined with other substances, such as therapeutic agents, in order to deliver such substances to the site of application or implantation of the polymeric fibers.

Accordingly, in one aspect, the present invention provides a device for the fabrication of a micron, submicron or nanometer dimension polymeric fiber. The device includes a rotary spinning system, the system comprising a rotating reservoir suitable for accepting a polymer and comprising an orifice for ejecting the polymer during rotation of the reservoir, thereby forming a micron, submicron or nanometer dimension polymeric fiber and a collector for accepting the formed micron, submicron or nanometer dimension polymeric fiber; wherein the device is free of an electrical field, e.g., a high voltage electrical field.

In another aspect, the present invention provides a device for the fabrication of a micron, submicron or nanometer dimension polymeric fiber. The device includes an oscillating track system, said system comprising a reservoir suitable for accepting a polymer and operably linked to the track system and comprising an orifice for ejecting said polymer during oscillation, e.g., vertical, horizontal, or diagonal oscillation, of the reservoir along the track system, thereby forming a micron, submicron or nanometer dimension polymeric fiber, and a collector for accepting said formed micron, submicron or nanometer dimension polymeric fiber, wherein the device is free of an electrical field, e.g., a high voltage electrical field.

A motor may be operably linked to the reservoir to provide rotation or oscillation to the reservoir. In one embodiment, the reservoir is operably linked to the shaft of a brushless motor. In another embodiment, the reservoir is operably linked to an oscillating motor.

Optionally, the devices may also include a supporting base which may house a power source and may also contain a speed control element for the rotating or oscillating reservoir. The devices may also optionally include a flexible air foil to facilitate the fiber collection.

In one embodiment, the device is depicted in FIG. 1(A). In another embodiment, the device is depicted in FIGS. 1(B) and 1(C). In yet another embodiment, the device is depicted in FIG. 2A.

The reservoir may contain one, two, three, four, five, six, seven, eight, nine, ten, eleven, twelve, thirteen, fourteen, fifteen, or more orifices, which may be of the same diameter or different diameters, e.g., about 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 micrometers.

The reservoir may also include a heating element for heating and/or melting the polymer.

The device may further comprise a component suitable for continuously feeding the polymer into the reservoir.

The collector of the device may be of any shape, e.g., round, oval, rectangular, or of a heart, kidney, lung, liver lobe(s), bladder, uterus, intestine, skeletal muscle or any other living organ shape, or portion thereof.

The reservoir and the collector of the device may be made up of a material that can withstand heat, or of a material that is not sensitive to chemical organic solvents. For example, the reservoir and the collector of the device may be made up of a plastic material, e.g., polypropylene, polyethylene, and polytetrafluoroethylene; or a metal, e.g., aluminum, steel, stainless steel, tungsten carbide, a tungsten alloy, titanium, and nickel.

In one embodiment of the invention, the device is free of a needle.

In another aspect, the invention provides methods for fabricating a micron, submicron or nanometer dimension polymeric fiber. The methods include continuously feeding a polymer into a rotating reservoir of a rotary spinning system which is substantially free of an electrical field; and rotating the system at a speed and for a time sufficient to form a micron, submicron or nanometer dimension polymeric fiber.

In another aspect, the invention provides methods for fabricating a micron, submicron or nanometer dimension polymeric fiber. The methods include continuously feeding a polymer into a reservoir of an oscillating track system which is substantially free of an electrical field, and oscillating the system at a speed and for a time sufficient to form a micron, submicron or nanometer dimension polymeric fiber.

The methods may further comprise collecting the formed micron, submicron or nanometer dimension polymeric fiber by, e.g., covering the formed micron, submicron or nanometer dimension polymeric fiber with a suitable material and peeling off the formed micron, submicron or nanometer dimension polymeric fiber from the walls of a collector of the rotary spinning system or the oscillating track system.

In one embodiment, the formed micron, submicron or nanometer dimension polymeric fiber is imaged, e.g., using a scanning electron microscope.

In certain embodiments of the invention, the rotary spinning system is rotated at a speed of, e.g., about 1,000 rpm to about 50,000 rpm, about 1,000 rpm to about 40,000 rpm, about 1,000 rpm to about 20,000 rpm, about 5,000 rpm to about 20,000 rpm, about 5,000 rpm to about 15,000 rpm, or about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, or about 24,000 rpm, for a time of, e.g., about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, about 100 minutes, or more.

In other embodiments of the invention, the oscillating track system is oscillated at a velocity of about of, e.g., about 650 millimeters/second (mm/sec) to about 33,000 mm/sec, about 650 mm/sec to about 26,000 mm/sec, 650 mm/sec to about 19,000 mm/sec, about 650 mm/sec to about 13,000 mm/sec, about 3,200 mm/sec to about 13,000 mm/sec, about 3,200 mm/sec to about 9,800 mm/sec, or about 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, 102,100, 10,200, 10,300, 10,400, 10,500, 10,600, 10,700, 10,800, 10,900, 11,000, 11,100, 11,200, 11,300, 11,400, 11,500, 11,600, 11,700, 11,800, 11,900, 12,000, 12,100, 12,200, 12,300, 12,400, 12,500, 12,600, 12,700, 12,800, 12,900, 13,000, 13,100, 13,200, 13,300, 13,400, 13,500, 13,600, 13,700, 13,800, 13,900, 14,000, 14,100, 14,200, 14,300, 14,400, 14,500, 14,600, 14,700, 14,800, 14,900, 15,000, 15,100, 15,200, 15,300, 15,400, 15,500, 15,600, 15,700, 15,800, 15,900, or about 16,000 mm/sec, for a time of, e.g., about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, about 100 minutes, or more.

The polymers for use in the methods of the invention may be biocompatible or nonbiocompatible and include, for example, poly(urethanes), poly(siloxanes) or silicones, poly (ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, polyorthoesters, polyesters, polyamides, polyolefins, polycarbonates, polyaramides, polyimides, and copolymers and derivatives thereof.

The polymers for use in the methods of the invention may also be naturally occurring polymers e.g., proteins, polysaccharides, lipids, nucleic acids or combinations thereof.

In one embodiment the polymers for use in the methods of the invention may be mixtures of two or more polymers and/or two or more copolymers. In one embodiment the polymers for use in the methods of the invention may be a mixture of one or more polymers and or more copolymers. In another embodiment, the polymers for use in the methods of the invention may be a mixture of one or more synthetic polymers and one or more naturally occurring polymers.

In one embodiment, the polymer is fed into the reservoir as a polymer solution, i.e., a polymer dissolved in an appropriate solution. In this embodiment, the methods may further comprise dissolving the polymer in a solvent prior to feeding the polymer into the reservoir. In other embodiments, the polymer is fed into the reservoir as a polymer melt. In such embodiment, the reservoir is heated at a temperature suitable for melting the polymer, e.g., is heated at a temperature of about 100° C. to about 300° C., 100-200° C., about 150-300° C., about 150-250° C., or about 150-200° C., or about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300° C.

In one embodiment of the invention, a plurality of micron, submicron or nanometer dimension polymeric fibers are formed. The plurality of micron, submicron or nanometer dimension polymeric fibers may be of the same diameter or of different diameters.

In one embodiment, the methods of the invention result in the fabrication of micron, submicron or nanometer dimension polymeric fiber having a diameter of about 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, 10, 20, 30, 40, or about 50 micrometers.

In one embodiment, the methods of the invention result in the fabrication of a plurality of aligned (e.g., uniaxially aligned) micron, submicron or nanometer dimension polymeric fibers.

In other embodiments of the invention, the plurality of micron, submicron or nanometer dimension polymeric fibers are contacted with additional agents, e.g., a plurality of living cells, e.g., muscle cells, neuron cells, endothelial cells, and epithelial cells; biologically active agents, e.g., lipophilic peptides, lipids, nucleotides; fluorescent molecules, metals, ceramics, nanoparticles, and pharmaceutically active agents.

In certain embodiments of the invention the polymeric fibers contacted with living cells are cultured in an appropriate medium for a time until, e.g., a living tissue is produced.

In still other embodiments, the polymer is contacted with living cells during the fabrication process such that fibers populated with cells or fibers surrounded (partially or totally) with cells are produced. The polymer may also be contacted with additional agents, such as proteins, nucleotides, lipids, drugs, pharmaceutically active agents, biocidal and antimicrobial agents during the fabrication process such that functional micron, submicron or nanometer dimension polymeric fibers are produced which contain these agents.

In other aspects, the present invention provides the polymeric fibers produced using the methods and devices of the invention, as well as tissues, membranes, filters, biological protective textiles, biosensor devices, food products, and drug delivery devices comprising the polymeric fibers of the invention.

In another aspect, the present invention provides methods for identifying a compound that modulates a tissue function. The methods include, providing a tissue produced according to the methods of the invention; contacting the tissue with a test compound; and determining the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound that modulates a tissue function.

In yet another aspect, the present invention provides methods for identifying a compound useful for treating or preventing a tissue disease. The methods include, providing a tissue produced according to the methods of the invention; contacting the tissue with a test compound; and determining the effect of the test compound on a tissue function in the presence and absence of the test compound, wherein a modulation of the tissue function in the presence of said test compound as compared to the tissue function in the absence of the test compound indicates that the test compound modulates a tissue function, thereby identifying a compound useful for treating or preventing a tissue disease.

The tissue function may be any suitable physiological activity associate with the particular tissue type, e.g., a biomechanical activity, e.g., contractility, cell stress, cell swelling, and rigidity, or an electrophysiological activity.

In one embodiment, the methods include applying a stimulus to the tissue.

In another embodiment, a plurality of living tissues are contacted with a test compound simultaneously.

The present invention is further illustrated by the following detailed description and drawings.

R.H.). (f) SEM of 5 wt % PEO in water spun at 12,000 rpm. (g) SEM of 8 wt % PAA in water at 50% neutralization degree spun at 12,000 rpm, (h) SEM of 8 wt % PAA in water at 100% neutralization degree spun at 12,000 rpm. (i) SEM of 14 wt % gelatin in 20 v/v % acetic acid spun at 12,000 rpm. (j) The laser scanning confocal image of fiber encapsulated fluorescent polystyrene beads (0.2 µm diameter). (k) SEM of emulsion of gelatin in PLA spun at 12,000 rpm rotation speed.

FIG. 3 depicts the effect of polymer concentration on the fabrication of 3D polymeric fibers with different features. (A) Using a 4% weight solution of polylactic acid (PLA) in chloroform at 10,000 rpm rotation speed beads are formed due to insufficient polymer entanglement and Rayleigh instability driven by surface tension forces. (B) Using a 6% weight solution of polylactic acid (PLA) in chloroform at 10,000 rpm rotation speed beads-on-string are formed due to insufficient polymer entanglement and Rayleigh instability driven by surface tension forces. (B') A graph depicting the size distribution of the average diameter of the nanofibers formed in (B). (C) Using an 8% weight solution of polylactic acid (PLA) in chloroform at 10,000 rpm rotation speed continuous fibers are formed. (C') A graph depicting the size distribution of the average diameter of the nanofibers formed in (C). (D) Using a 10% weight solution of polylactic acid (PLA) in chloroform at 10,000 rpm rotation speed continuous fibers with a bimodal distribution of diameters are formed. (D') A graph depicting the size distribution of the average diameter of the nanofibers formed in (D).

Figure 4:
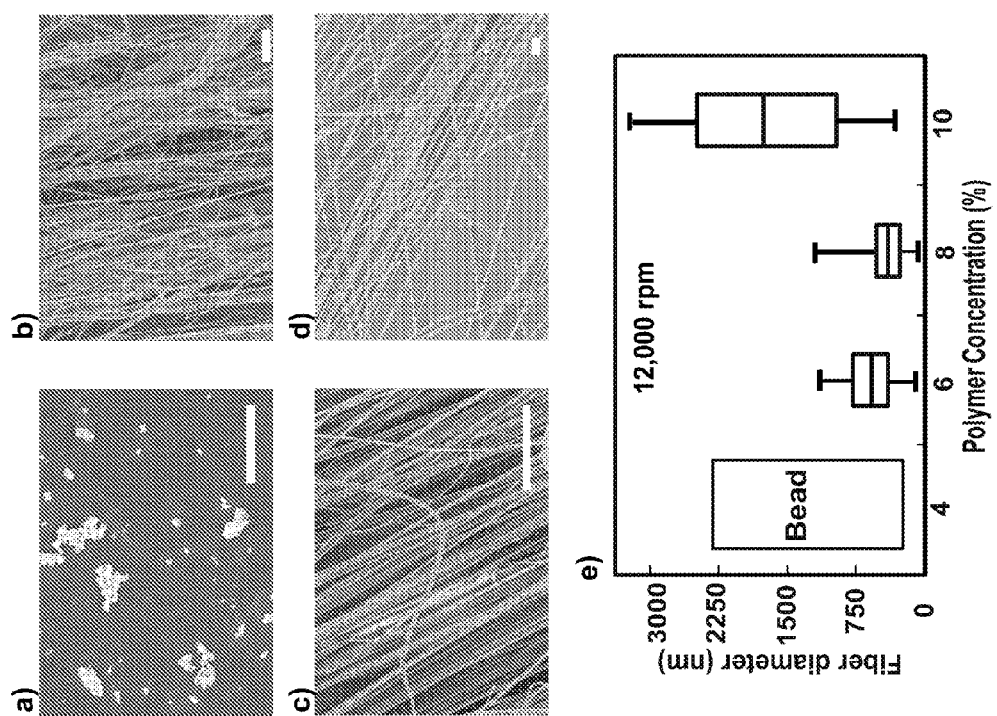

FIG. 4 depicts fiber morphology and the diameter distribution for 8% weight PLA solution spun at different rotation speeds. At the top, scanning electron micrographs show the morphology of fibers spun at 4,000 rpm, 8,000 rpm, and 12,000 rpm rotation speed. The graph plots the diameters of fibers formed. The horizontal lines inside the boxes in the graph represent the median values and the limits of the box denote the upper and lower quartiles. The maximum and minimum values are delimited by the bars. Scale bar is 10 micrometers for all scanning electron micrographs.

Figures 5A, 5B:
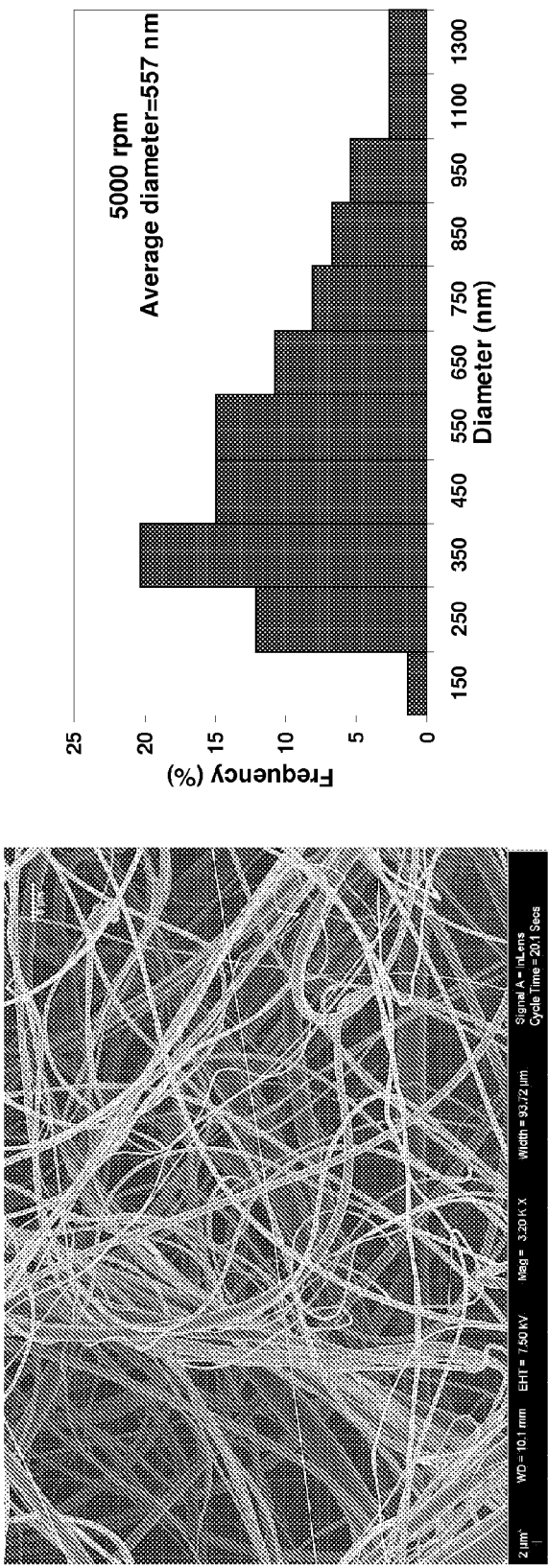

FIG. 5(A) depicts a scanning electron micrograph of fibers fabricated at 5,000 rpm rotation speed. FIG. 5(B) is a graph depicting the diameter distribution of at least 200 samples of produced fibers showing that the average diameter is 557 nm.

Figure 6B:
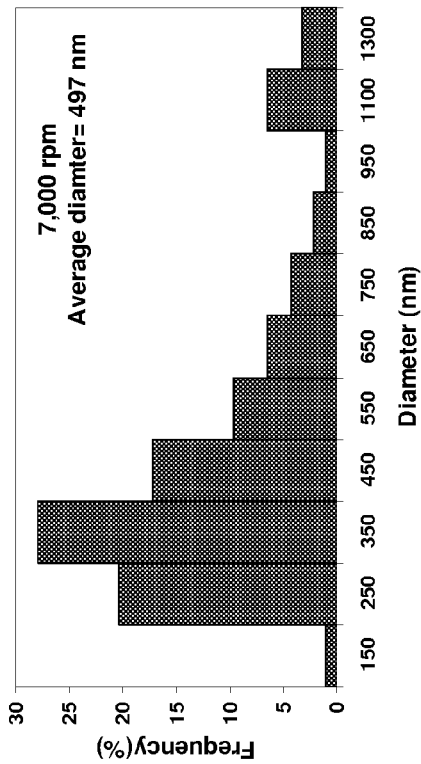
Figure 6A:
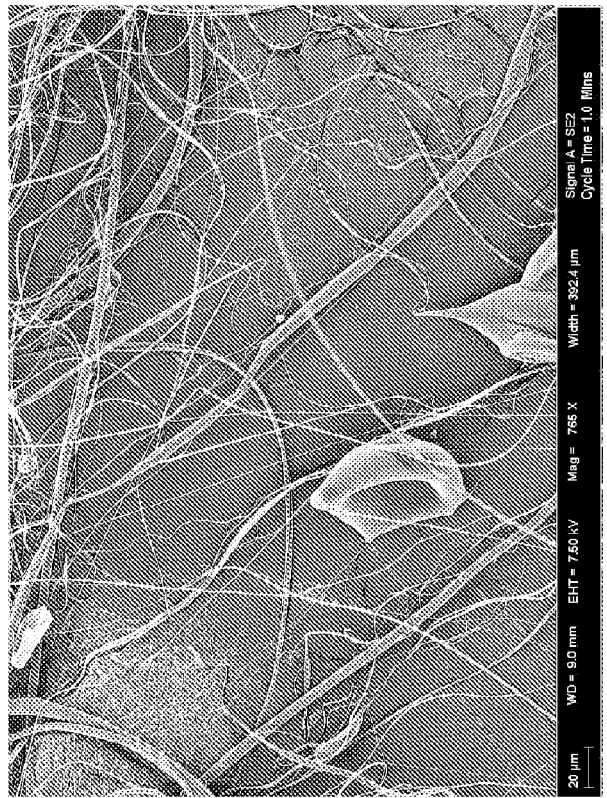

FIG. 6(A) depicts a scanning electron micrograph of fibers fabricated at 7,000 rpm rotation speed. FIG. 6(B) is a graph depicting the diameter distribution of at least 200 samples of produced fibers showing that the average diameter is 497 nm.

Figures 7A, 7B:
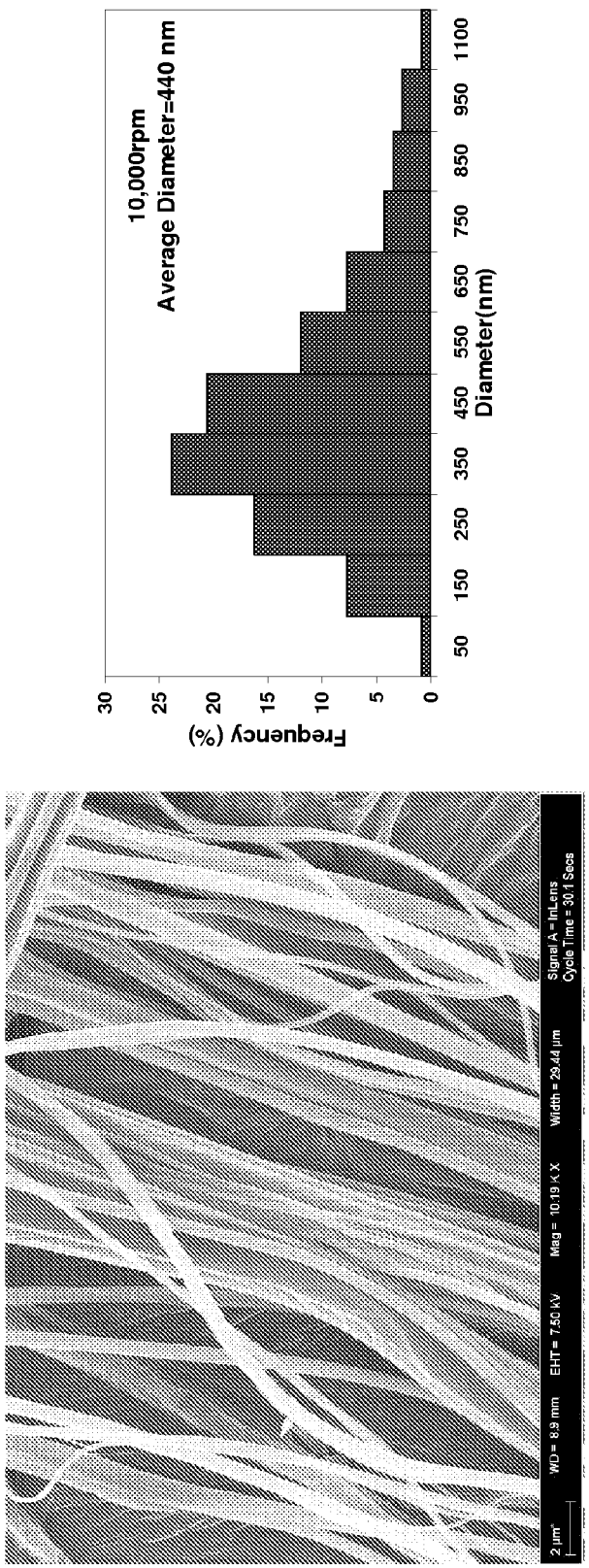

FIG. 7(A) depicts a scanning electron micrograph of fibers fabricated at 10,000 rpm rotation speed. FIG. 7(B) is a graph depicting the diameter distribution of at least 200 samples of produced fibers showing that the average diameter is 440 nm.

Figure 8:
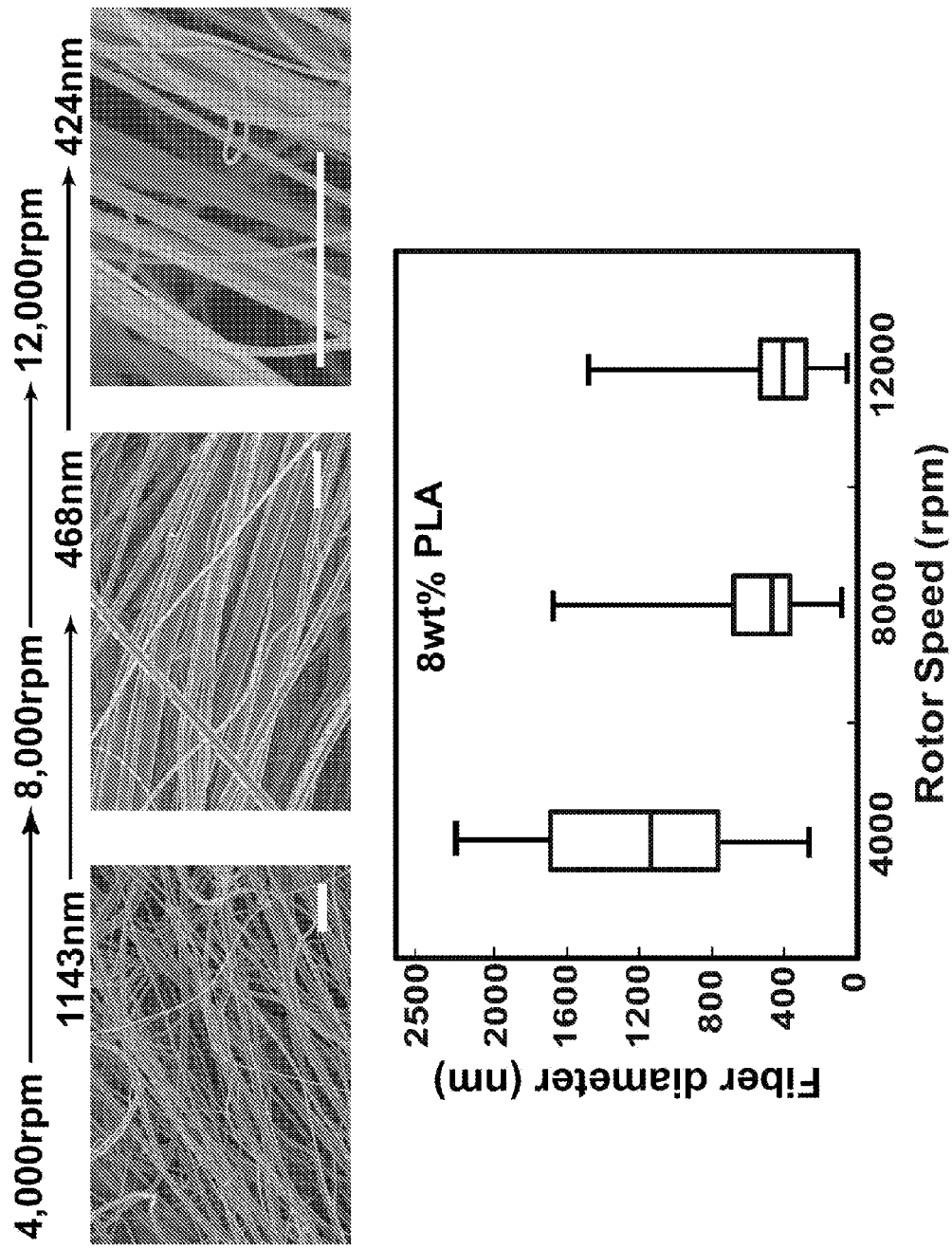

FIG. 8 depicts fiber morphology and the diameter distribution for 4%, 6%, 8%, and 10% weight PLA solutions spun at 12,000 rpm rotation speed. At the top, scanning electron micrographs show the morphology of fibers fabricated using 4% (a), 6% (b), 8% (c), and 10% (d) weight PLA solutions. The graph plots the diameters of fibers formed. The horizontal lines inside the boxes in the graph represent the median values and the limits of the box denote the upper and lower quartiles. The maximum and minimum values are delimited by the bars. Scale bar is 20 micrometers for all scanning electron micrographs.

Figure 9:
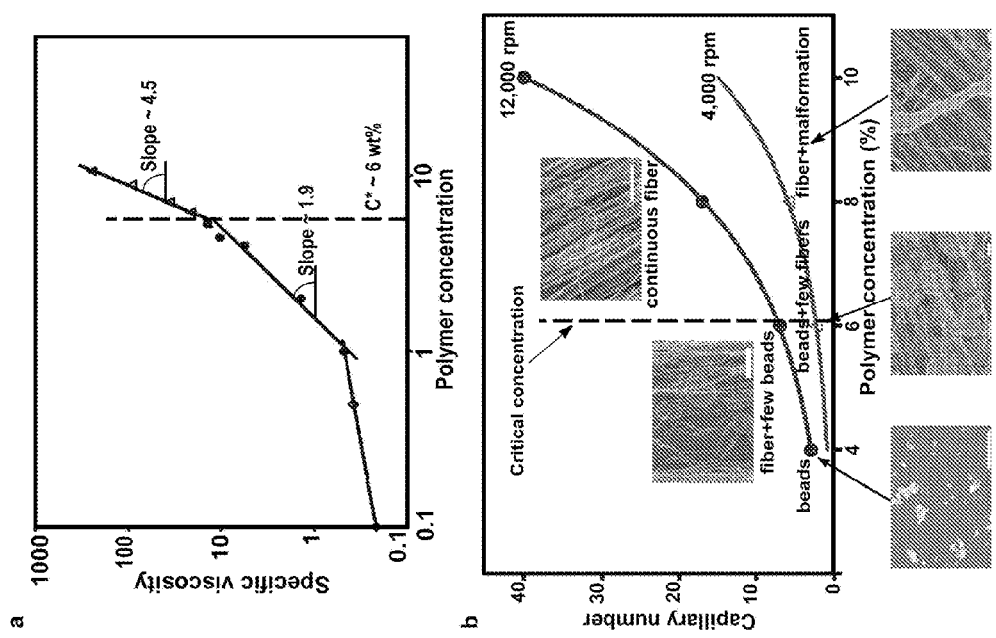

FIG. 9$a$ is a graph depicting the specific viscosity of polymer solutions versus polymer concentration for PLA solutions in chloroform. Changes in the slope mark the onset of the semi-dilute, unentangled, semi-dilute, entangled, and concentrated regimes. The concentrated regime (c*) was found to be 6% weight. FIG. 9$b$ is a graph depicting the relationship between capillary number, polymer concentration and fiber morphology of fibers fabricated at various rotation speeds. The critical polymer concentration and critical capillary number indicated. The jet break-up may be estimated by the capillary number, defined as the ratio of Weber number (We) to Reynolds number (Re), which characterizes the ratio of the viscous force to the surface tension force. Scale bar is 20 µm.

Figure 10:
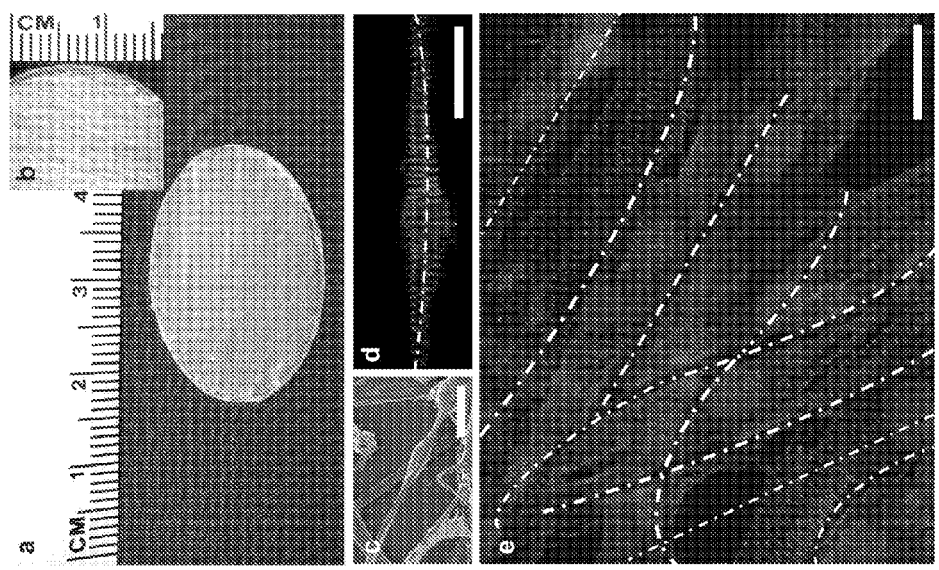

FIG. 10 depicts the use of the polymeric fibers prepared using the devices and methods as described herein for fabrication of tissue engineered scaffolds. (a) Photographic image of PLA scaffold affixed to a 25 mm glass coverslip. (b) Stereo microscope image of PLA scaffold shows macroscale alignment of fibers. (c) SEM of PLA fibers with a cell attached to and encompassing the fiber bundle. Median fiber diameter is 1.43±0.55 µm. (d) Laser scanning confocal image of a cardiomyocyte attached to and extending along a gelatin nanofiber. Median diameter of gelatin fibers is 515±27 nm (white dashed line). (e) Laser scanning confocal image of engineered anisotropic cardiac muscle on a RJS-produced PLA scaffold (fibers are 1.43±0.55 µm diameter, white dashed lines). Nuclear DNA is stained in light gray, α-actinin at the sarcomeric Z-lines is medium gray. Scale bars are 20 µm.

Figure 11:
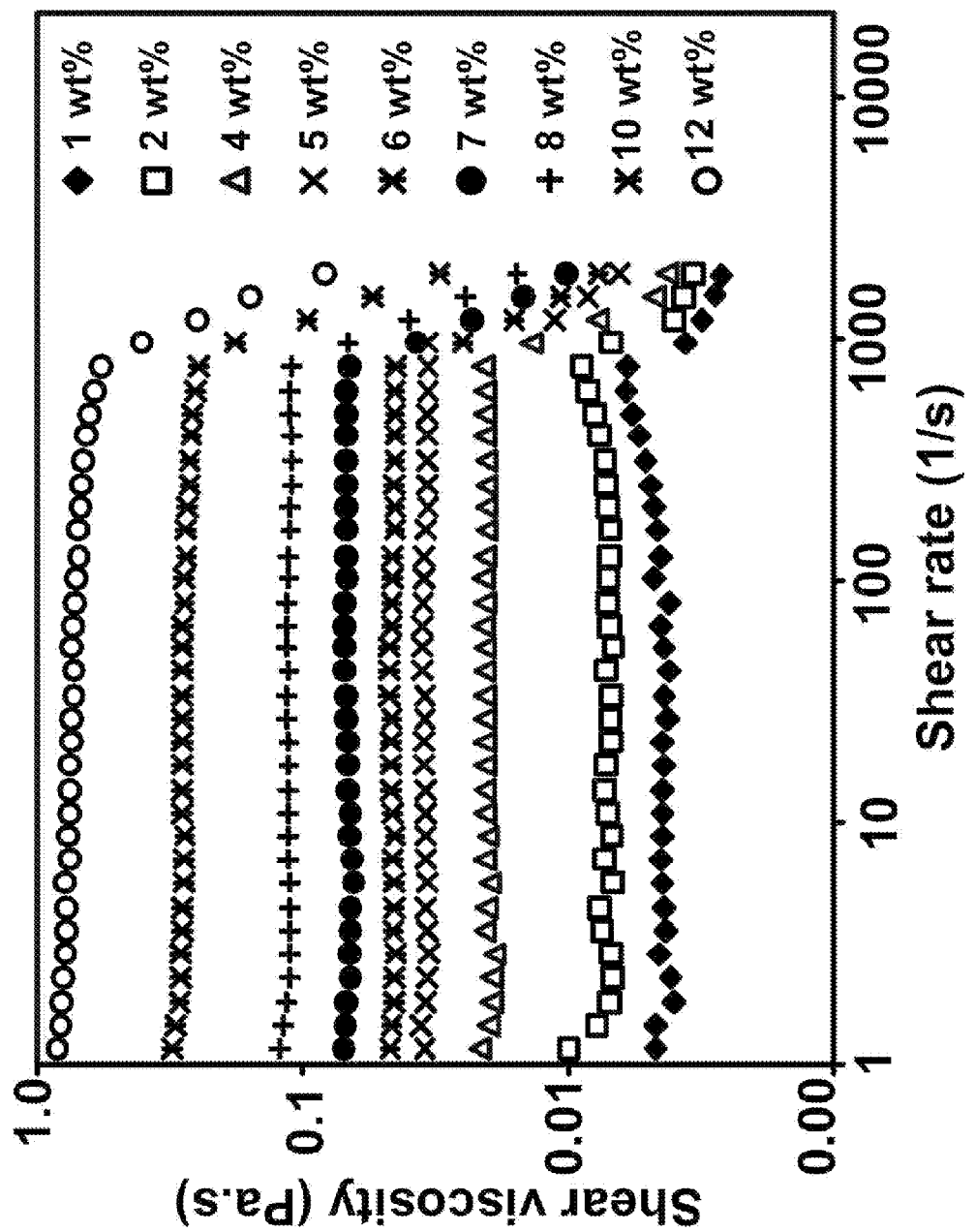

FIG. 11 is a graph plotting viscosity as a function of shear rate for different concentrations of PLA.

DETAILED DESCRIPTION OF THE INVENTION

Described herein are improved methods and devices for the fabrication of polymeric fibers. The polymeric fibers produced according to the methods disclosed herein can be, for example, used as extracellular matrix and, together with cells, may also be used in forming engineered tissue. Such tissue is useful not only for the production of prosthetic devices and regenerative medicine, but also for investigating tissue developmental biology and disease pathology, as well as in drug discovery and toxicity testing. The polymeric fibers of the invention may also be combined with other substances, such as, therapeutic agents, in order to deliver such substances to the site of application or implantation of the polymeric fibers. The polymeric fibers produced according to the methods disclosed herein may also be used to generate food products, membranes and filters.

I. Devices and Methods of the Invention

In one embodiment, the devices disclosed herein allow for tunable polymeric fiber orientation, alignment, and diameter by applying centrifugal actions and without use of an electrical field, e.g., a high voltage electrical field. In another embodiment, the devices disclosed herein allow for tunable polymeric fiber orientation, alignment, and diameter by applying oscillating actions and without use of an electrical field, e.g., a high voltage electrical field.

Figure 1A:
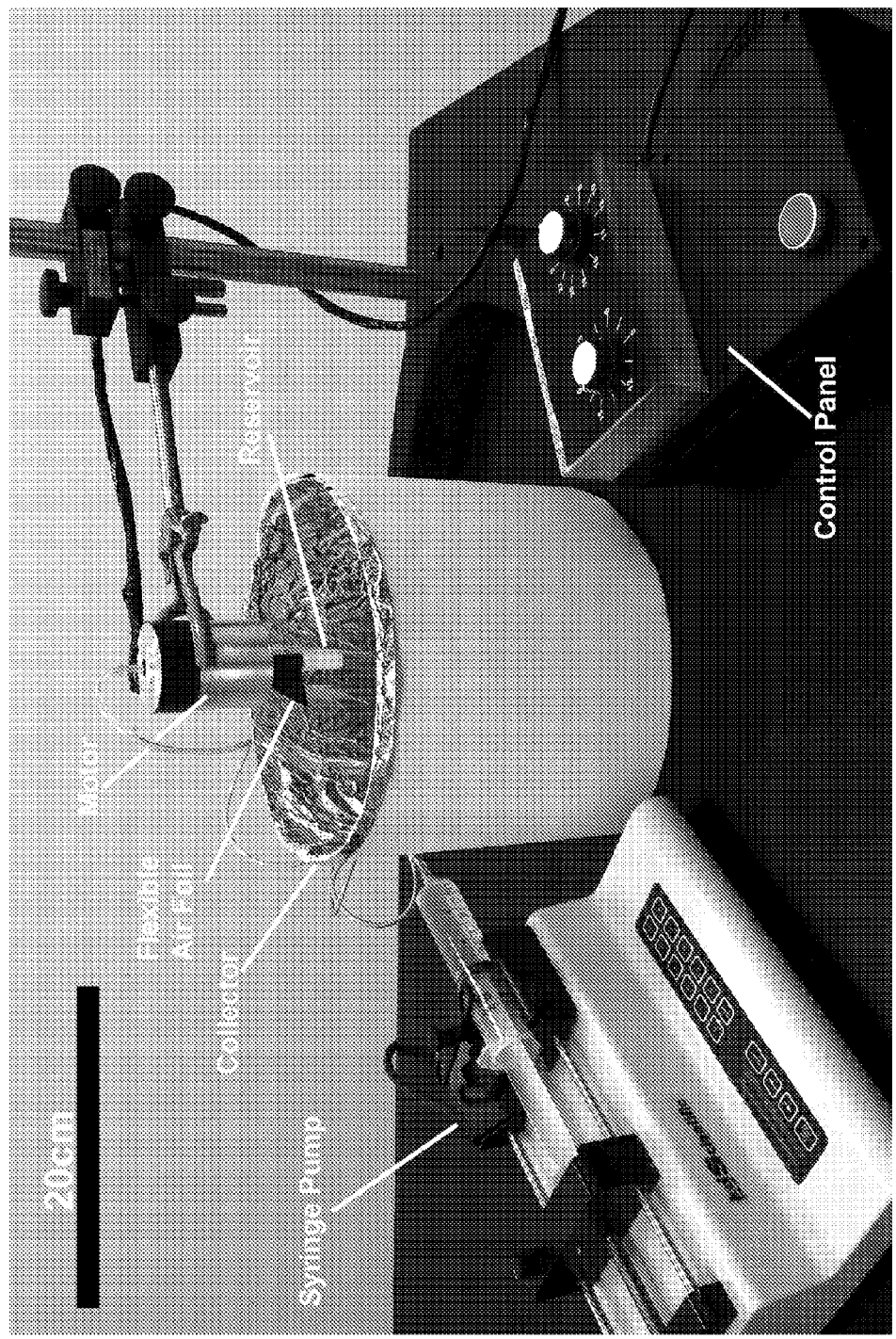
FIG. 1 depicts an aspect of the devices of the invention. (A) Photograph of a device. (B) Schematic representation of one embodiment of the devices of the invention. (C) Enlarged schematic representation of the device in 1(B) showing that the polymer solution is ejected from the two orifices of the rotating reservoir due to centrifugal action.
Figure 1C:
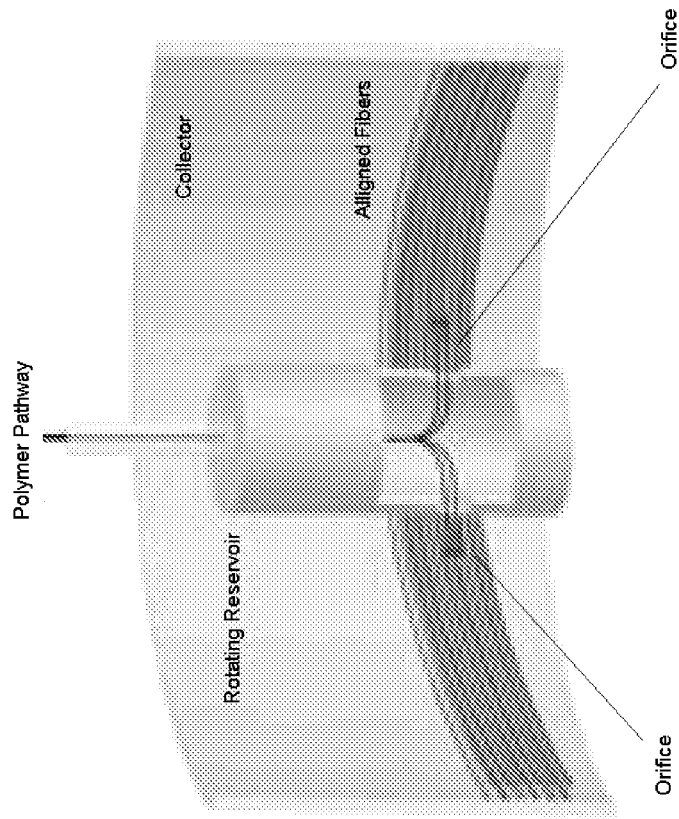

In one aspect, the present invention provides devices, e.g., devices for the fabrication of a polymeric fiber, such as a polymeric fiber having a micron, submicron, or nanometer dimension. An exemplary device of the invention is shown in FIG. 1A. In one embodiment, the devices of the invention are comprised of a rotary spinning system, which includes a rotating reservoir suitable for accepting a polymer and comprising an orifice for ejecting the polymer during rotation of the reservoir, thereby forming a polymeric fiber and a collector for accepting the formed polymeric fiber. In another embodiment, the devices are comprised of an oscillating track system which is operably linked to a reservoir suitable for accepting a polymer and comprising an orifice for ejecting the polymer during oscillation of the reservoir, thereby forming a polymeric fiber and a collector for accepting the formed polymeric fiber.

The devices of the invention may also comprise a motor and a power source to produce rotation or oscillation. In one embodiment, the rotary spinning system comprises a motor and a power source. In one embodiment, the reservoir is operably linked to the shaft of a motor, e.g., a brushless motor. In one embodiment, the oscillating track system comprises a track, a motor, and a power source. The track may comprise one or more belts and/or gears operably linked to form the track. Suitable motors are known in the art and one of ordinary skill in the art would be able to select an appropriate motor.

In one embodiment, the devices are substantially void of an electric field, or do not require, an electrical field, e.g., a high voltage electrical field, in order to generate the polymeric fiber. In another embodiment, the devices are free of a needle. Optionally, the devices may also include a supporting base which may house a power source and may also contain a speed control element for rotating or oscillating the reservoir.

The rotating comprises sufficient orifices for ejecting the polymer during rotation or oscillation of the reservoir, such as 1, 2, 3, 4, 5, 6, 7, 8, 9, 10, 11, 12, 13, 14, 15, or more orifices. The orifices may be of the same diameter or of different diameters, e.g., diameters of about 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or about 1000 micrometers. Diameters intermediate to the above-recited values are also intended to be part of this invention.

Any suitable size or geometrically shaped reservoir or collector may be used in the devices of the invention. For example, the reservoir may be round, rectangular, or oval. The collector may be round, oval, rectangular, or a half-heart shape. The collector may also be shaped in the form of any living organ, such as a heart, kidney, liver lobe(s), bladder, uterus, intestine, skeletal muscle, or lung shape, or portion thereof. The collector may further be shaped as any hollow cavity, organ or tissue, such as a circular muscle structure, e.g., a sphincter or iris.

These shapes allow the polymeric fibers to be deposited in the form of a living organ for the production of engineered tissue and organs, described in more detail below.

The reservoir and collector may be constructed of any material, e.g., a material that can withstand heat and/or that is not sensitive to chemical organic solvents. In one embodiment, the reservoir and the collector are made up of a plastic material, e.g., polypropylene, polyethylene, or polytetrafluoroethylene. In another embodiment, the reservoir and the collector are made up of a metal, e.g., aluminum, steel, stainless steel, tungsten carbide, tungsten alloys, titanium or nickel.

In certain embodiments, the collector is maintained at about room temperature, e.g., about 20, 21, 22, 23, 24, 25, 26, 27, 28, 29, or about 30° C. and ambient humidity, e.g., about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or about 90% humidity.

Figure 1B:
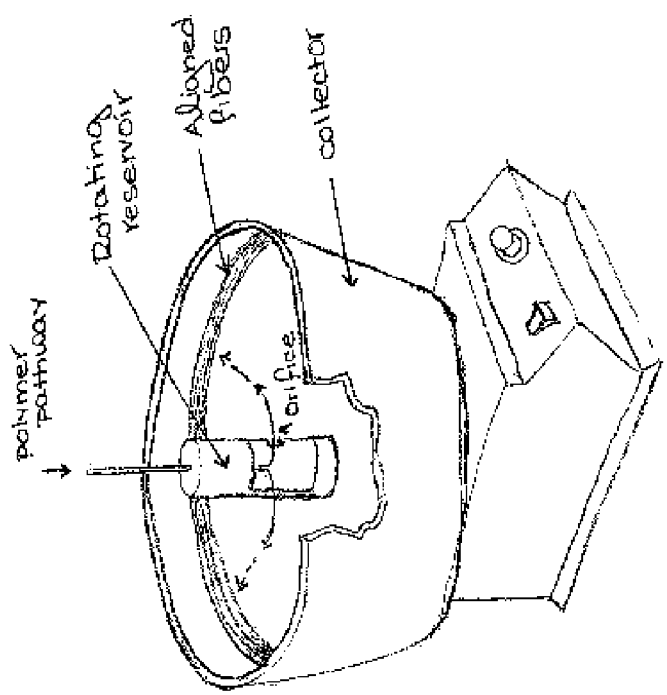

In one embodiment, the device of the invention further comprises a component suitable for continuously feeding the polymer into the rotating reservoir, such as a spout or syringe pump as depicted in FIGS. 1(A) and 1(B).

The present invention also provides methods for fabricating polymeric fibers, e.g., a micron, submicron, or nanometer polymeric fibers. In one embodiment, the methods include continuously feeding a polymer into a rotating reservoir of a rotary spinning system which is substantially free of an electrical field, and rotating the system at a speed and for a time sufficient to form polymeric fibers. In another embodiment, the methods include continuously feeding a polymer into an oscillating reservoir of an oscillating track system which is substantially free of an electrical field, and rotating the system at a speed and for a time sufficient to form polymeric fibers. The methods of the invention may further comprise collecting the formed polymeric fiber by, for example, covering the formed polymeric fiber with a material (such as aluminum foil) and peeling off the formed polymeric fiber from the walls of the collector of the spinning rotary system or oscillating track system. Optionally, the polymeric fibers may be imaged using, e.g., a scanning electron microscope.

Figure 2:
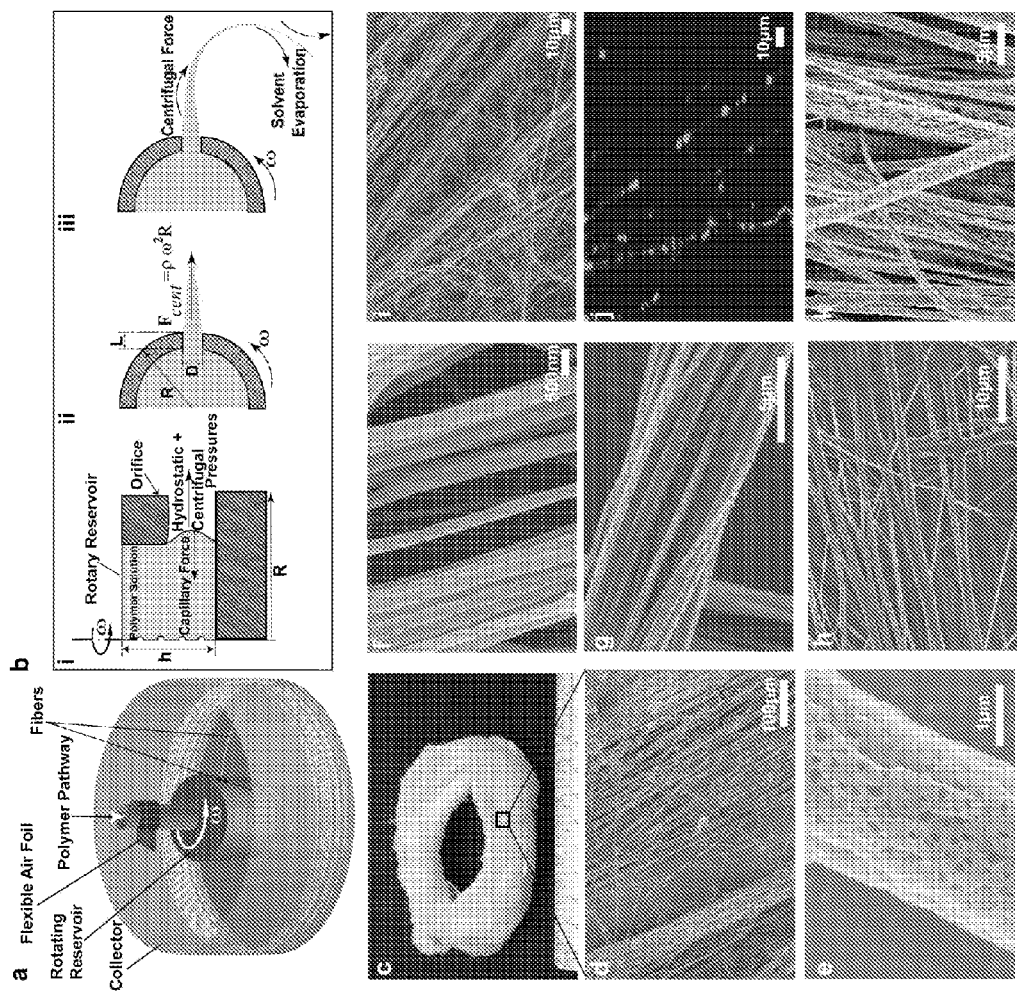
FIG. 2 depicts a schematic of one aspect of the invention, referred to as a rotary jet-spinning process (RJS). (a) In one embodiment, a rotary jet-spinning device includes a perforated reservoir (internal volume of 700 µL and external diameter of 12.5 mm) with two side wall orifices (orifice diameter of 340 µm and length to diameter ratio of 9) which rotates about its vertical axis in the center of a stationary collector; the polymer solution continuously feeds into the reservoir and produces fibers that are deposited over the collector (diameter of 300 mm). (b) Without wishing to be bound by theory, this figure depicts a magnified view of the formation mechanism of polymeric fibers using the RJS system depicted in (a), (i) jet-initiation, (ii) jet-extension and (iii) solvent evaporation. (c) Photographic image of 3D polymeric fiber produced by rotary jet-spinning, 8 wt % PLA in CHCl3 at 12,000 rpm rotation speed. (d) Scanning electron micrograph (SEM) of fibers in 2(c). (e) PLA fibers (10 wt % PLA in CHCl3 at 12,000 rpm rotation speed) produced with expedited solvent evaporation and high humidity (more than 55%

In certain embodiments of the invention, the methods include mixing a biologically active agent, e.g., a polypeptide, protein, nucleic acid molecule, nucleotide, lipid, biocide, antimicrobial, or pharmaceutically active agent, with the polymer during the fabrication process of the polymeric fibers. For example, as depicted in FIG. 2j polymeric fibers prepared using the devices and methods of the invention were contacted with encapsulated fluorescent polystyrene beads.

In other embodiments, a plurality of living cells is mixed with the polymer during the fabrication process of the polymeric fibers. In such embodiments, biocompatible polymers (e.g., hydrogels) may be used.

Sufficient speeds and times for rotating the rotary spinning system or oscillating the oscillating track system to form a polymeric fiber are dependent on the concentration of the polymer and the desired features of the formed polymeric fiber. For example, as shown in the Examples, an 8% weight solution of polylactic acid rotated at 10,000 rpm allowed the formation of continuous polymeric fibers.

Accordingly, in one embodiment, the rotary spinning system may be rotated at a speed of about 1,000 rpm-50,000 rpm, about 1,000 rpm to about 40,000 rpm, about 1,000 rpm to about 20,000 rpm, about 5,000 rpm-20,000 rpm, about 5,000 rpm to about 15,000 rpm, or about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, or about 24,000 rpm. Ranges and values intermediate o the above recited ranges and values are also contemplated to be part of the invention. For example, rotating speeds of about 10,000 rpm-15,000 rpm, or 8,000 rpm-12,000 rpm are intended to be encompassed by the methods of the invention. In one embodiment, the rotary spinning system may be rotated at a speed greater than about 1,000 rpm, greater than about 1,500 rpm, greater than about 2,000 rpm, greater than about 2,500 rpm, greater than about 3,000 rpm, greater than about 3,050 rpm, greater than about 3,100 rpm, greater than about 3,150 rpm, greater than about 3,200 rpm, greater than about 3,250 rpm, greater than about 3,300 rpm, greater than about 3,350 rpm, greater than about 3,400 rpm, greater than about 3,450 rpm, greater than about 3,500 rpm, greater than about 3,550 rpm, greater than about 3,600 rpm, greater than about 3,650 rpm, greater than about 3,700 rpm, greater than about 3,750 rpm, greater than about 3,800 rpm, greater than about 3,850 rpm, greater than about 3,900 rpm, greater than about 3,950 rpm, or greater than about 4,000 rpm.

The rotary spinning system may be rotated for a time sufficient to form a desired polymeric fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

In other embodiments of the invention, the oscillating track system is oscillated at a velocity of about of, e.g., about 650 millimeters/second (mm/sec) to about 33,000 mm/sec, about 650 mm/sec to about 26,000 mm/sec, 650 mm/sec to about 19,000 mm/sec, about 650 mm/sec to about 13,000 mm/sec, about 3,200 mm/sec to about 13,000 mm/sec, about 3,200 mm/sec to about 9,800 mm/sec, or about 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, 102,100, 10,200, 10,300, 10,400, 10,500, 10,600, 10,700, 10,800, 10,900, 11,000, 11,100, 11,200, 11,300, 11,400, 11,500, 11,600, 11,700, 11,800, 11,900, 12,000, 12,100, 12,200, 12,300, 12,400, 12,500, 12,600, 12,700, 12,800, 12,900, 13,000, 13,100, 13,200, 13,300, 13,400, 13,500, 13,600, 13,700, 13,800, 13,900, 14,000, 14,100, 14,200, 14,300, 14,400, 14,500, 14,600, 14,700, 14,800, 14,900, 15,000, 15,100, 15,200, 15,300, 15,400, 15,500, 15,600, 15,700, 15,800, 15,900, or about 16,000 mm/sec. Ranges and values intermediate o the above recited ranges and values are also contemplated to be part of the invention. For example, rotating speeds of about 6,500 mm/sec-9,800 mm/sec, or 5,200 mm/sec-7,800 mm/sec rpm are intended to be encompassed by the methods of the invention.

The oscillating track system may be oscillated for a time sufficient to form a desired polymeric fiber, such as, for example, about 1 minute to about 100 minutes, about 1 minute to about 60 minutes, about 10 minutes to about 60 minutes, about 30 minutes to about 60 minutes, about 1 minute to about 30 minutes, about 20 minutes to about 50 minutes, about 5 minutes to about 20 minutes, about 5 minutes to about 30 minutes, or about 15 minutes to about 30 minutes, about 5-100 minutes, about 10-100 minutes, about 20-100 minutes, about 30-100 minutes, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, or more. Times and ranges intermediate to the above-recited values are also intended to be part of this invention.

Any polymer may be used to fabricate the polymeric fibers of the invention.

In one embodiment, the polymer is not sugar, e.g., raw sugar, or sucrose. In another embodiment, the polymer is not floss sugar.

In one embodiment, a polymer for use in the methods of the invention is a synthetic polymer. In one embodiment, the polymer is biocompatible. Suitable biocompatible polymers, include, but are not limited to, for example, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, and polyorthoesters, and copolymers and derivatives thereof.

In another embodiment, polymers for use in the polymeric fibers of the invention are not biocompatible. Suitable non-biocompatible polymers, include, but are not limited to, for example, polyesters, polyamides, polyolefins, polycarbonates, polyaramides, polyimides, and copolymers and derivatives thereof.

In yet another embodiment, polymers for use in the polymeric fibers of the invention are naturally occurring polymers. Non-limiting examples of such naturally occurring polymers include, for example, polypeptides, proteins, e.g., capable of fibrillogenesis, polysaccharides, e.g., alginate, lipids, nucleic acid molecules, and combinations thereof.

In one embodiment, a single polymer is used to fabricate the polymeric fibers of the invention. In another embodiment, two, three, four, five, or more polymers are used to fabricate the polymeric fibers of the invention. In one embodiment the polymers for use in the methods of the invention may be mixtures of two or more polymers and/or two or more copolymers. In one embodiment the polymers for use in the methods of the invention may be a mixture of one or more polymers and or more copolymers. In another embodiment, the polymers for use in the methods of the invention may be a mixture of one or more synthetic polymers and one or more naturally occurring polymers.

A polymer for use in the methods of the invention may be fed into the reservoir as a polymer solution. Accordingly, the methods of the invention may further comprise dissolving the polymer in a solvent (e.g., chloroform, water, ethanol, isopropanol) prior to feeding the polymer into the reservoir.

Alternatively, the polymer may be fed into the reservoir as a polymer melt and, thus, in one embodiment, the reservoir is heated at a temperature suitable for melting the polymer, e.g., heated at a temperature of about 100° C.-300° C., 100° C.-200° C., about 150-300° C., about 150-250° C., or about 150-200° C., 200° C.-250° C., 225° C.-275° C., 220° C.-250° C., or about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or about 300° C. Ranges and temperatures intermediate to the recited temperature ranges are also part of the invention. In such embodiments, the reservoir may further comprise a heating element.

The devices and methods of the invention may be used to form a single, continuous polymeric fiber or a plurality of polymeric fibers of the same or different diameters, e.g., diameters about 25 nanometers to about 50 micrometers, about 100 nanometers to about 1 micrometer, about 500 nanometers to about 100 micrometers, 25 micrometers to about 100 micrometers, or about 5, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, 10, 20, 30, 40, or about 50 micrometers. Sizes and ranges intermediate to the recited diameters are also part of the invention.

The polymeric fibers formed using the methods and devices of the invention may be of any length. In one embodiment, the length of the polymeric fibers is dependent on the length of time the device is rotated or oscillated and/or the amount of polymer fed into the system. For example, the polymeric fibers may be about 1 nanometer, about 10 feet, or about 500 yards. Additionally, the polymeric fibers may be cut to a desired length using any suitable instrument.

In one embodiment, the methods and device of the invention produce about 0.5, 1, 2, 3, 4, 5, 6, 7, 8, 9, 10, 11, 12, 13, 14, or about 15 grams of polymeric fiber per hour.

In one embodiment, the polymeric fibers formed according to the methods of the invention are further contacted with an agent to produce or increase the size of pores or number of pores per surface unit area in the polymeric fibers.

The polymeric fibers formed according to the methods of the invention may be contacted with additional agents and optionally cultured in an appropriate medium, such as a tissue culture medium. Contacting the polymeric fibers with the additional agents will allow the agents to, for example, coat (fully or partially) the fibers, or in the case of for example cells, to intercalate between fibers. Contacting the polymer with additional agents during the fabrication of the polymeric fibers also allows the agents to be incorporated into the polymeric fibers themselves.

In one embodiment, a plurality of polymeric fibers may be contacted, e.g., seeded, with a plurality of living cells, e.g., vascular smooth muscle cells, myocytes (e.g., cardiac myocytes), skeletal muscle, myofibroblasts, airway smooth muscle cells, osteoblasts, myoblasts, neuroblasts, fibroblasts, glioblasts, germ cells, hepatocytes, chondrocytes, keratinocytes, connective tissue cells, glial cells, epithelial cells, endothelial cells, vascular endothelial cells, hormone-secreting cells, cells of the immune system, neural cells, and cells that will differentiate into contractile cells (e.g., stem cells, e.g., embryonic stem cells or adult stem cells, progenitor cells or satellite cells). In one embodiment, polymeric fibers treated with a plurality of living cells may be cultured in an appropriate medium in vitro. Such cultured cells exhibit characteristics and functions typical of such cells in vivo. The plurality of living cells may comprise one or more types of cells, such as described in U.S. Provisional Application No. 61/306,736 and PCT Application No. PCT/US09/060,224, entitled "Tissue Engineered Mycocardium and Methods of Productions and Uses Thereof", filed Oct. 9, 2009, the entire contents of each of which are incorporated herein by reference.

The cells may be normal cells, abnormal cells (e.g., those derived from a diseased tissue, or those that are physically or genetically altered to achieve a abnormal or pathological phenotype or function), normal or diseased muscle cells derived from embryonic stem cells or induced pluripotent stem cells.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. PCT/US09/060,224, entitled "Tissue Engineered Myocardium and Methods of Productions and Uses Thereof", filed Oct. 9, 2009, the entire contents of which are incorporated herein by reference.

Cells for seeding can be cultured in vitro, derived from a natural source, genetically engineered, or produced by any other means. Any natural source of prokaryotic or eukaryotic cells may be used. Embodiments in which the polymeric fibers contacted with a plurality of living cells are implanted in an organism can use cells from the recipient, cells from a conspecific donor or a donor from a different species, or bacteria or microbial cells.

In one embodiment of the invention, a plurality of polymeric fibers is contacted with a plurality of muscle cells and cultured such that a living tissue is produced.

In another embodiment of the invention, a plurality of polymeric fibers is contacted with a plurality of muscle cells and cultured such that a living tissue is produced, and the living tissue is further contacted with neurons, and cultured such that a living tissue with embedded neural networks is produced.

In one particular embodiment, the living tissue is an anisotropic tissue, e.g., a muscle thin film.

In other embodiments of the invention, a plurality of polymeric fibers is contacted with a biologically active polypeptide or protein, such as, collagen, fibrin, elastin, laminin, fibronectin, integrin, hyaluronic acid, chondroitin 4-sulfate, chondroitin 6-sulfate, dermatan sulfate, heparin sulfate, heparin, and keratan sulfate, and proteoglycans. In one embodiment, the polypeptide or protein is lipophilic.

In still other embodiments, the polymeric fibers are contacted with nucleic acid molecules and/or nucleotides, or lipids.

A plurality of polymeric fibers may also be contacted with a pharmaceutically active agent. Suitable pharmaceutically active agents include, for example, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, or monoamine oxidase inhibitors.

Other suitable pharmaceutically active agents include growth factors and cytokines. Growth factors useful in the present invention include, but are not limited to, transforming growth factor-α ("TGF-α"), transforming growth factor-β ("TGF-β"), platelet-derived growth factors including the AA, AB and BB isoforms ("PDGF"), fibroblast growth factors ("FGF"), including FGF acidic isoforms 1 and 2, FGF basic form 2, and FGF 4, 8, 9 and 10, nerve growth factors ("NGF") including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof.

Other agents that may be used to contact the polymeric fibers of the invention, include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, amino acids, peptides, polypeptides, and proteins, e.g., structural proteins, enzymes, and peptide hormones.

For agents such as nucleic acids, any nucleic acid can be used to contact the polymeric fibers. Examples include, but are not limited to deoxyribonucleic acid (DNA), ent-DNA, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat.

Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the polymeric fibers. The nucleic acids can be in any form that is effective to enhance uptake into cells.

Agents used to treat the polymeric fibers of the invention may also be cell fragments, cell debris, organelles and other cell components, tablets, and viruses as well as vesicles, liposomes, capsules, nanoparticles, and other agents that serve as an enclosure for molecules. In some embodiments, the agents constitute vesicles, liposomes, capsules, or other enclosures that contain agents that are released at a time after contacting, such as at the time of implantation or upon later stimulation or interaction. In one illustrative embodiment, transfection agents such as liposomes contain desired nucleotide sequences to be incorporated into cells that are located in or on the polymeric fibers.

Magnetically or electrically reactive materials are examples of other agents that are optionally used to contact the polymeric fibers of the present invention. Examples of magnetically active materials include but are not limited to ferrofluids (colloidal suspensions of magnetic particles), and various dispersions of electrically conducting polymers. Ferrofluids containing particles approximately 10 nanometers in diameter, polymer-encapsulated magnetic particles about 1-2 microns in diameter, and polymers with a glass transition temperature below room temperature are particularly useful. Examples of electrically active materials are polymers including, but not limited to, electrically conducting polymers such as polyanilines and polypyrroles, ionically conducting polymers such as sulfonated polyacrylamides are related materials, and electrical conductors such as carbon black, graphite, carbon nanotubes, metal particles, and metal-coated plastic or ceramic materials.

Suitable biocides for contacting the polymeric fibers of the invention, include, but are not limited to, organotins, brominated salicylanilides, mercaptans, quaternary ammonium compounds, mercury compounds, and compounds of copper and arsenic.

Antimicrobial agents, which include antibacterial agents, antiviral agents, antifungal agents, and antiparisitic agents, may also be used to contact the polymeric fibers of the invention.

The present invention is also directed to the polymeric fibers produced using the methods and device of the invention, as well as, tissues, membranes, filters, and drug delivery device, e.g., polymeric fibers treated with, e.g., a pharmaceutically active agent, comprising the polymeric fibers of the invention.

II. Use of the Polymeric Fibers of the Invention

The polymeric fibers of the invention may be used in a broad range of applications, including, but not limited to, manufacture of engineered tissue and organs, including structures such as patches or plugs of tissues or matrix material, prosthetics, and other implants, tissue scaffolding for, e.g., fractal neural and/or vascular networks, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, catalytic substrates, photonics, filtration, protective clothing, cell scaffolding, drug delivery, wound healing, food products, and numerous other uses.

For example, in one embodiment, the polymeric fibers of the invention may be used to prepare a membrane, which is useful as, for example, a dressing for wounds or injuries of any type. Stem cells, fibroblasts, epithelial cells, and/or endothelial cells may be included to allow tissue growth. Such use of the polymeric fibers may be combined with other methods of treatment, repair, and contouring.

In another embodiment, a polymeric fiber membrane can be inserted as a filler material into wounds to enhance healing by providing a substrate that does not have to be synthesized by fibroblasts and other cells, thereby decreasing healing time and reducing the metabolic energy requirement to synthesize new tissue at the site of the wound.

Several uses of polymeric fiber membranes are possible in the field of surgical repair or construction. For example, membranes of the present invention may be used to make tissue or orthopedic screws, plates, sutures, or sealants that are made of the same material as the tissue in which the devices will be used.

In other exemplary embodiments, polymeric fiber membranes may be used to form, e.g., a sleeve to use as reinforcement for aneurysms or at the site of an anastamosis. Such sleeves are placed over the area at which reinforcement is desired and sutured, sealed, or otherwise attached to the vessel. Polymeric fiber membranes may also be used as hemostatic patches and plugs for leaks of cerebrospinal fluid. Yet another use is as an obstruction of the punctum lacryma for a patient suffering from dry eye syndrome.

Polymeric fiber membranes may also be used to support or connect tissue or structures that have experienced injury, surgery, or deterioration. For example, such membranes may be used in a bladder neck suspension procedure for patients suffering from postpartum incontinence. Rectal support, vaginal support, hernia patches, and repair of a prolapsed uterus are other illustrative uses. The membranes may be used to repair or reinforce weakened or dysfunctional sphincter muscles, such as the esophageal sphincter in the case of esophageal reflux. Other examples include reinforcing and replacing tissue in vocal cords, epiglottis, and trachea after removal, such as in removal of cancerous tissue.

Other uses for the membranes of the invention include, for example, preparing an obstruction or reinforcement for an obstruction to a leak. For example, to seal openings in lungs after lung volume reduction (partial removal).

Another exemplary us of the polymeric fibers of the invention is as a barrier for the prevention of post-operative induced adhesion(s).

Yet another exemplary use of the polymeric fibers of the invention is to serve as a template for nerve growth.

In another embodiment of the invention, the polymeric fibers may be used to prepare a filter. Such filters are useful for filtration of contaminants, biological agents and hazardous but very small particles, e.g., nanoparticles. For example, a polymeric fiber filter of the invention may be used to purify liquids, such as water, e.g., drinking water, oil, e.g., when used in an automobile oil filter. In another embodiment, a polymeric fiber filter may be used to purify air when used in, e.g., a face mask, to filter out viruses, bacteria and hazardous nanoparticles.

The polymeric fibers of the invention may also be incorporated into biosensor devices, e.g., a device that uses a biological element (e.g., enzyme, antibody, whole cell, etc.) to monitor the presence of various chemicals on a substrate by enabling highly specific interactions between biological molecules to be detected and utilized, e.g., as a biorecognition surface. Such biosensors may be used in various applications such as the monitoring of pollutants in water, air, and soil, and in the detection of medically important molecules such as hormones, sugars, and peptides in body fluids, and for pathogen detection.

In yet other embodiments of the invention, the polymeric fibers may be used to prepare textiles. In one embodiment, the textile are biological protective textiles, e.g., textiles that provide protection from toxic agents, e.g., biological and chemical toxins. For example, the polymeric fibers may include, e.g., chlorhexidine, which can kill most bacteria, or an oxime that can break down organophosphates, chemicals that are the basis of many pesticides, insecticides and nerve gases.

In another embodiment, the polymeric fibers of the invention may be used to prepare food products. For example, polymeric fibers may be made of an edible polymer, e.g., alginate, to which a flavoring, e.g., fruit flavoring or chocolate, may be added. In one embodiment, the food product is not cotton candy.

Another use of the polymeric fibers of the present invention is the delivery of one or more substances to a desired location and/or in a controlled manner. In some embodiments, the polymeric fibers are used to deliver the materials, e.g., a pharmaceutically active substance. In other embodiments, the polymeric fibers materials are used to deliver substances that are contained in the polymeric fibers or that are produced or released by substances contained in the polymeric fibers materials. For example, polymeric fibers containing cells can be implanted in a body and used to deliver molecules produced by the cells after implantation. The present compositions can be used to deliver substances to an in vivo location, an in vitro location, or other locations. The present compositions can be applied or administered to these locations using any method.

The ability to seed the polymeric fibers of the invention with living cells also provides the ability to build tissue, organs, or organ-like tissues. Cells included in such tissues or organs can include cells that serve a function of delivering a substance, seeded cells that will provide the beginnings of replacement tissue, or both.

In one embodiment of the invention, a plurality of polymeric fibers are treated with a plurality of living cells and cultured under appropriate conditions to produce a bioengineered tissue.

In some embodiments, polymeric fibers contacted or seeded with living cells are combined with a drug such that the function of the implant will improve. For example, antibiotics, anti-inflammatories, local anesthetics or combinations thereof, can be added to the cell-treated polymeric fibers of a bioengineered organ to speed the healing process.

Examples of bioengineered tissue include, but are not limited to, bone, dental structures, joints, cartilage, (including, but not limited to articular cartilage), skeletal muscle, smooth muscle, cardiac muscle, tendons, menisci, ligaments, blood vessels, stents, heart valves, corneas, ear drums, nerve guides, tissue or organ patches or sealants, a filler for missing tissues, sheets for cosmetic repairs, skin (sheets with cells added to make a skin equivalent), soft tissue structures of the throat such as trachea, epiglottis, and vocal cords, other cartilaginous structures such as articular cartilage, nasal cartilage, tarsal plates, tracheal rings, thyroid cartilage, and arytenoid cartilage, connective tissue, vascular grafts and components thereof, and sheets for topical applications, and repair of organs such as livers, kidneys, lungs, intestines, pancreas visual system, auditory system, nervous system, and musculoskeletal system.

In one particular embodiment, a plurality of polymeric fibers are contacted with a plurality of living muscle cells and cultured under appropriate conditions to guide cell growth with desired anisotropy to produce a muscle thin film (MTF) or a plurality of MTFs prepared as described in PCT Publication No. WO 2008/051265 and U.S. Provisional Application No. 61/174,511, entitled "High Throughput Assays for Determining Muscle Cell Function and Devices for Use Therein", filed, May 1, 209, the entire contents of each of which are incorporated herein by reference.

Polymeric fibers contacted with living cells can also be used to produce prosthetic organs or parts of organs. Mixing of committed cell lines in a three dimensional polymeric fiber matrix can be used to produce structures that mimic complex organs. The ability to shape the polymeric fibers allows for preparation of complex structures to replace organs such as liver lobes, pancreas, other endocrine glands, and kidneys. In such cases, cells are implanted to assume the function of the cells in the organs. Preferably, autologous cells or stem cells are used to minimize the possibility of immune rejection.

In some embodiments, polymeric fibers contacted with living cells are used to prepare partial replacements or augmentations. For example, in certain disease states, organs are scarred to the point of being dysfunctional. A classic example is hepatic cirrhosis. In cirrhosis, normal hepatocytes are trapped in fibrous bands of scar tissue. In one embodiment of the invention, the liver is biopsied, viable liver cells are obtained, cultured in a plurality of polymeric fibers, and re-implanted in the patient as a bridge to or replacement for routine liver transplantations.

In another example, by growing glucagon secreting cells, insulin secreting cells, somatostatin secreting cells, and/or pancreatic polypeptide secreting cells, or combinations thereof, in separate cultures, and then mixing them together with polymeric fibers, an artificial pancreatic islet is created. These structures are then placed under the skin, retroperitoneally, intrahepatically or in other desirable locations, as implantable, long-term treatments for diabetes.

In other examples, hormone-producing cells are used, for example, to replace anterior pituitary cells to affect synthesis and secretion of growth hormone secretion, luteinizing hormone, follicle stimulating hormone, prolactin and thyroid stimulating hormone, among others. Gonadal cells, such as Leydig cells and follicular cells are employed to supplement testosterone or estrogen levels. Specially designed combinations are useful in hormone replacement therapy in post and perimenopausal women, or in men following decline in endogenous testosterone secretion. Dopamine-producing neurons are used and implanted in a matrix to supplement defective or damaged dopamine cells in the substantia nigra. In some embodiments, stem cells from the recipient or a donor can be mixed with slightly damaged cells, for example pancreatic islet cells, or hepatocytes, and placed in a plurality of polymeric fibers and later harvested to control the differentiation of the stem cells into a desired cell type. In other embodiments thyroid cells can be seeded and grown to form small thyroid hormone secreting structures. This procedure is performed in vitro or in vivo. The newly formed differentiated cells are introduced into the patient.

Bioengineered tissues are also useful for measuring tissue activities or functions, investigating tissue developmental biology and disease pathology, as well as in drug discovery and toxicity testing.

Accordingly, the present invention also provides methods for identifying a compound that modulates a tissue function. The methods include providing a bioengineered tissue produced according to the methods of the invention, such as a muscle thin film; contacting the bioengineered tissue with a test compound; and determining the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound that modulates a tissue function.

In another aspect, the present invention also provides methods for identifying a compound useful for treating or preventing a disease. The methods include providing a bioengineered tissue produced according to the methods of the invention, e.g., a muscle thin film; contacting a bioengineered tissue with a test compound; and determining the effect of the test compound on a tissue function in the presence and absence of the test compound, wherein a modulation of the tissue function in the presence of the test compound as compared to the tissue function in the absence of the test compound indicates that the test compound modulates a tissue function, thereby identifying a compound useful for treating or preventing a disease.

The methods of the invention generally comprise determining the effect of a test compound on an bioengineered tissue as a whole, however, the methods of the invention may comprise further evaluating the effect of a test compound on an individual cell type(s) of the bioengineered tissue.

The methods of the invention may involve contacting a single bioengineered tissue with a test compound or a plurality of bioengineered tissues with a test compound.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a bioengineered tissue with a test compound) is intended to include any form of interaction (e.g., direct or indirect interaction) of a test compound and a bioengineered tissue. The term contacting includes incubating a compound and a bioengineered tissue (e.g., adding the test compound to a bioengineered tissue).

Test compounds, may be any agents including chemical agents (such as toxins), small molecules, pharmaceuticals, peptides, proteins (such as antibodies, cytokines, enzymes, and the like), and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to a bioengineered tissue by any suitable means. For example, the test compound may be added drop-wise onto the surface of a bioengineered tissue of the invention and allowed to diffuse into or otherwise enter the bioengineered tissue, or it can be added to the nutrient medium and allowed to diffuse through the medium. In the embodiment where the bioengineered tissue is cultured in a multi-well plate, each of the culture wells may be contacted with a different test compound or the same test compound. In one embodiment, the screening platform includes a microfluidics handling system to deliver a test compound and simulate exposure of the microvasculature to drug delivery.

Numerous physiologically relevant parameters, e.g., insulin secretion, conductivity, neurotransmitter release, lipid production, bile secretion, e.g., muscle activities, e.g., biomechanical and electrophysiological activities, can be evaluated using the polymeric fiber tissues of the invention. For example, in one embodiment, the polymeric fiber tissues of the present invention can be used in contractility assays for muscular cells or tissues, such as chemically and/or electrically stimulated contraction of vascular, airway or gut smooth muscle, cardiac muscle or skeletal muscle. In addition, the differential contractility of different muscle cell types to the same stimulus (e.g., pharmacological and/or electrical) can be studied.

In another embodiment, the bioengineered tissues of the present invention can be used for measurements of solid stress due to osmotic swelling of cells. For example, as the cells swell the polymeric fiber tissues will bend and as a result, volume changes, force and points of rupture due to cell swelling can be measured.

In another embodiment, the bioengineered tissues of the present invention can be used for pre-stress or residual stress measurements in cells. For example, vascular smooth muscle cell remodeling due to long term contraction in the presence of endothelin-1 can be studied.

Further still, the bioengineered tissues of the present invention can be used to study the loss of rigidity in tissue structure after traumatic injury, e.g., traumatic brain injury. Traumatic stress can be applied to vascular smooth muscle bioengineered tissues as a model of vasospasm. These bioengineered tissues can be used to determine what forces are necessary to cause vascular smooth muscle to enter a hyper-contracted state. These bioengineered tissues can also be used to test drugs suitable for minimizing vasospasm response or improving post-injury response and returning vascular smooth muscle contractility to normal levels more rapidly.

In other embodiments, the bioengineered tissues of the present invention can be used to study biomechanical responses to paracrine released factors (e.g., vascular smooth muscle dilation due to release of nitric oxide from vascular endothelial cells, or cardiac myocyte dilation due to release of nitric oxide).

In other embodiments, the bioengineered tissues of the invention can be used to evaluate the effects of a test compound on an electrophysiological parameter, e.g., an electrophysiological profile comprising a voltage parameter selected from the group consisting of action potential, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release. For example, a decrease in a voltage or calcium flux parameter of a bioengineered tissue comprising cardiomyocytes upon contacting the bioengineered tissue with a test compound, would be an indication that the test compound is cardiotoxic.

In yet another embodiment, the bioengineered tissues of the present invention can be used in pharmacological assays for measuring the effect of a test compound on the stress state of a tissue. For example, the assays may involve determining the effect of a drug on tissue stress and structural remodeling of the bioengineered tissues. In addition, the assays may involve determining the effect of a drug on cytoskeletal structure and, thus, the contractility of the bioengineered tissues.

In still other embodiments, the bioengineered tissues of the present invention can be used to measure the influence of biomaterials on a biomechanical response. For example, differential contraction of vascular smooth muscle remodeling due to variation in material properties (e.g., stiffness, surface topography, surface chemistry or geometric patterning) of bioengineered tissues can be studied.

In further embodiments, the bioengineered tissues of the present invention can be used to study functional differentiation of stem cells (e.g., pluripotent stem cells, multipotent stem cells, induced pluripotent stem cells, and progenitor cells of embryonic, fetal, neonatal, juvenile and adult origin) into contractile phenotypes. For example, the polymeric fibers of the invention are treated with undifferentiated cells, e.g., stem cells, and differentiation into a contractile phenotype is observed by thin film bending. Differentiation can be observed as a function of: co-culture (e.g., co-culture with differentiated cells), paracrine signaling, pharmacology, electrical stimulation, magnetic stimulation, thermal fluctuation, transfection with specific genes and biomechanical perturbation (e.g., cyclic and/or static strains)

In another embodiment, the bioengineered tissues of the invention may be used to determine the toxicity of a test compound by evaluating, e.g., the effect of the compound on an electrophysiological response of a bioengineered tissue. For example, opening of calcium channels results in influx of calcium ions into the cell, which plays an important role in excitation-contraction coupling in cardiac and skeletal muscle fibers. The reversal potential for calcium is positive, so calcium current is almost always inward, resulting in an action potential plateau in many excitable cells. These channels are the target of therapeutic intervention, e.g., calcium channel blocker sub-type of anti-hypertensive drugs. Candidate drugs may be tested in the electrophysiological characterization assays described herein to identify those compounds that may potentially cause adverse clinical effects, e.g., unacceptable changes in cardiac excitation, that may lead to arrhythmia.

For example, unacceptable changes in cardiac excitation that may lead to arrhythmia include, e.g., blockage of ion channel requisite for normal action potential conduction, e.g., a drug that blocks $Na^+$ channel would block the action potential and no upstroke would be visible; a drug that blocks $Ca^{2+}$ channels would prolong repolarization and increase the refractory period; blockage of $K^+$ channels would block rapid repolarization, and, thus, would be dominated by slower $Ca^{2+}$ channel mediated repolarization.

In addition, metabolic changes may be assessed to determine whether a test compound is toxic by determining, e.g., whether contacting a bioengineered tissue with a test compound results in a decrease in metabolic activity and/or cell death. For example, detection of metabolic changes may be measured using a variety of detectable label systems such as fluormetric/chrmogenic detection or detection of bioluminescence using, e.g., AlamarBlue fluorescent/chromogenic determination of REDOX activity (Invitrogen), REDOX indicator changes from oxidized (non-fluorescent, blue) state to reduced state (fluorescent, red) in metabolically active cells; Vybrant MTT chromogenic determination of metabolic activity (Invitrogen), water soluble MTT reduced to insoluble formazan in metabolically active cells; and Cyquant NF fluorescent measurement of cellular DNA content (Invitrogen), fluorescent DNA dye enters cell with assistance from permeation agent and binds nuclear chromatin. For bioluminescent assays, the following exemplary reagents is used: Cell-Titer Glo luciferase-based ATP measurement (Promega), a thermally stable firefly luciferase glows in the presence of soluble ATP released from metabolically active cells.

The bioengineered tissues of the invention are also useful for evaluating the effects of particular delivery vehicles for therapeutic agents e.g., to compare the effects of the same agent administered via different delivery systems, or simply to assess whether a delivery vehicle itself (e.g., a viral vector or a liposome) is capable of affecting the biological activity of the bioengineered tissue. These delivery vehicles may be of any form, from conventional pharmaceutical formulations, to gene delivery vehicles. For example, the devices of the invention may be used to compare the therapeutic effect of the same agent administered by two or more different delivery systems (e.g., a depot formulation and a controlled release formulation). The bioengineered tissues of the invention may also be used to investigate whether a particular vehicle may have effects of itself on the tissue. As the use of gene-based therapeutics increases, the safety issues associated with the various possible delivery systems become increasingly important. Thus, the bioengineered tissues of the present invention may be used to investigate the properties of delivery systems for nucleic acid therapeutics, such as naked DNA or RNA, viral vectors (e.g., retroviral or adenoviral vectors), liposomes and the like. Thus, the test compound may be a delivery vehicle of any appropriate type with or without any associated therapeutic agent.

Furthermore, the bioengineered tissues of the present invention are a suitable in vitro model for evaluation of test compounds for therapeutic activity with respect to, e.g., a muscular and/or neuromuscular disease or disorder. For example, the bioengineered tissues of the present invention (e.g., comprising muscle cells) may be contacted with a candidate compound by, e.g., immersion in a bath of media containing the test compound, and the effect of the test compound on a tissue activity (e.g., a biomechanical and/or electrophysiological activity) may measured as described herein, as compared to an appropriate control, e.g., an untreated bioengineered tissue. Alternatively, a bioengineered tissue of the invention may be bathed in a medium containing a candidate compound, and then the cells are washed, prior to measuring a tissue activity (e.g., a biomechanical and/or electrophysiological activity) as described herein. Any alteration to an activity determined using the bioengineered tissue in the presence of the test agent (as compared to the same activity using the device in the absence of the test compound) is an indication that the test compound may be useful for treating or preventing a tissue disease, e.g., a neuromuscular disease.

Additional contemplated uses of the polymeric fibers of the invention are disclosed in, for example, PCT Publication Nos.: WO 2008/045506, WO 2003/099230, and WO 2004/032713, the entire contents of which are incorporated herein by reference.

This invention is further illustrated by the following examples which should not be construed as limiting. The contents of all references, patents and published patent applications cited throughout this application, as well as the Figures, are hereby incorporated by reference.

EXAMPLES

Materials and Methods

The following materials and methods were used in the Examples below.

Polymers and Solvents

A variety of synthetic and naturally occurring polymers including polyethylene oxide (PEO, Mv=1,000 kD Sigma-Aldrich, Milwaukee, Wis.), gelatin type A from Sigma, poly (lactic acid) (PLA polymer 2002D, NatureWorks®, Minnetonka, Minn.) with a melt index of 4-8 g/10 min (ASTM D1238) and poly(acrylic acid) (PAA, Mv=450 kD, Sigma-Aldrich) were used. Chloroform (99.9% HPLC grade), hydrochloric acid, sodium hydroxide, and acetic acid (glacial) were purchased from Sigma-Aldrich (Milwaukee, Wis.) and dimethylformamide (98.5%) was purchased from VWR (San Dimas, CA). Fluorescent Microspheres (FluoSpheres®, 2% solid suspension, 0.2 μm diameter) was purchased from Molecular Probes, Inc. (Eugene, Oreg.). All reagents were used as received without further purification.

Fabrication

A. Solution preparation: PEO was dissolved at a concentration of 5 wt % in deionized (18 Ω/cm) water (Millipore, Billerica, Mass.) at room temperature. Gelatin powder was dissolved at a concentration of 14 wt % in 20 v/v % acetic acid at 30° C. PAA at a concentration of 8 wt % was dissolved in deionized water at room temperature and then neutralized with sodium hydroxide to reach both half and full neutralized states. PLA was dissolved in chloroform at varied concentration of 4-10 wt % at room temperature. To prepare polymer emulsions, gelatin solution was added slowly to 8 wt % PLA in chloroform in the ratio of 1:50 (vol.) and vortexed for 5 min prior to RJS. For microsphere encapsulated samples, 10 μL of microsphere suspension was added under dark conditions to PEO solution and vortexed for 10 min. prior to RJS. The concentration of beads was 5-6×10$^6$ per ml of polymer solution. For tissue engineering studies, PLA was dissolved at concentrations of 8 wt % in chloroform:dimethylformamide (80:20) before fiber fabrication.

B. Fiber fabrication: The RJS system consisted of a polypropylene reservoir with a diameter of 12.5 mm and height of 25.4 mm (FIG. 1A). The reservoir had two sidewall orifices with diameter (D) of 340 μm and L:D ratio of 9, where L is the orifice length depicted in FIG. 2b. The perforated reservoir was attached to the shaft of a brushless motor (model BND23 from Peromatic GmbH, Switzerland) and rotation speed was controlled by a circuit board. The circuit is equipped with a manual rotation speed control to change the rotation of the motor before or during RJS. The polymer solution was continuously fed to the reservoir via polyethylene tube connected to a 50 ml syringe placed in the cradle of syringe pump (KD Scientific, Holliston, Mass.). Rotation started immediately after filling the reservoir. The resulting fibers were collected on a stationary round collector. Collected fibers were removed and weighed after certain period of time to evaluate production rate. The production rate was 5-6 grams/hour which is ~10 times higher than the production rate of standard electro spinning. To study effect of orifice geometry on fiber geometry, another orifice with diameter of 650 μm and L:D ratio of 5 was built.

C. Preparation of fibrous scaffold for cell culture: Fibrous scaffolds from PLA and gelatin were prepared as described above and were affixed to 25 mm glass coverslips using polydimethylsiloxane adhesive at the edges. After sample mounting, gelatin nanofibers were cross-linked by exposing to vapor of 4 ml gluteraldehyde in a 9 cm×10 cm×12 cm sealed container for 12 hours. Following cross-linking, samples were allowed to dry overnight to vaporize any remnant gluteraldehyde, and rinsed with 1×PBS. Samples were then sterilized by soaking in ethanol with exposure to a germicidal lamp in a laminar flow hood for 8 hours. After sterilization, PLA fibers were incubated in 50 μg/ml fibronectin solution for 24 hours and rinsed with 1×PBS before cell culturing.

D. Cell culture: Neonatal rat left ventricular cardiomyocytes were isolated from 2-day old neonatal Sprague-Dawley rats as previously reported (Feinberg, A. W., et al. (2007) *Science* 317(5843):1366-1370). All procedures were approved by the Harvard Animal Care and Use Committee. Reagents were obtained from Sigma unless otherwise indicated. Ventricles were surgically isolated and homogenized by washing in Hanks balanced salt solution followed by digestion with trypsin and collagenase with agitation overnight at 4° C. Subsequently, cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 U/mL penicillin and seeded onto the nanofiber scaffolds at a density of 350,000 cells/mL. Samples were incubated under standard conditions at 37° C. and 5% $CO_2$. After an additional 48 hours the media was exchanged with maintenance media (M199 media supplemented as above but with 2% FBS) to minimize growth of fibroblasts inevitably present in the primary harvest cardiomyocyte population.

Sample Characterization

A. Viscosity Measurements: Rheological measurements were made on freshly prepared PLA solutions for determining the concentration regimes. PLA solutions ranging from 0.1 to 12 wt % were loaded into the viscometer (Model AR-G2, TA instruments, New Castle, Del.) fitted with a cone and plate spindle (model 987864, 40 mm cone diameter, 3°, 59', 56" cone angle and 109 μm gap) and viscosities were measured under steady state shear rate from 0.1-3.000 s$^{-1}$. All PLA solutions showed Newtonian behavior over low range of shear rates; however, it should be noted that shear thinning occurred at higher shear rates. The zero-shear viscosity ($\eta_0$) was determined over the Newtonian region. FIG. 11, shows the flow behavior of PLA solutions ranging from 0.1 to 12 wt % at variable shear rates. The critical polymer concentration was calculated based on the zero-shear viscosities over the Newtonian region. The polymer contribution to the $\eta_0$ was studied by defining the specific viscosity ($\eta_{sp}$) in:

$$\text{Specific viscosity } (\eta_{sp}) = \frac{\eta_0 - \eta_s}{\eta_s} \tag{S1}$$

where $\eta_s$ is solvent viscosity. The $\eta_{sp}$ is plotted as a function of concentration in FIG. 9a for the PLA solutions. Changes in the slope marked the onset of the semidilute unentangled, semidilute entangled and concentrated regimes (Wang, C., et al. (2009) *Polymer* 50(25):6100-6110). The concentrated regime (c*) was found to be 6 wt %.

B. Surface tension measurement: The surface tension of the polymer solution was measured based on Du Nouy ring method with Sigma700 Tensiometer (KSV instruments) (Grant, J., et al. (2008) *Biomacromolecules* 9(8):2146-2152).

C. Scanning Electron Microscopy: Fiber samples removed from the collector and mounted on sample stubs and coated with Pt/Pd using a sputter coater (Denton Vacuum, Moorestown, N.J.) to minimize charging during imaging. The samples were imaged using Zeiss Ultra field-emission scanning electron microscope (Carl Zeiss, Dresden, Germany). Images were acquired and analyzed using image analysis software (Image J, National Institutes of Health, US). A total of 100-300 fibers were analyzed (5 random fields of view per sample) to determine the fiber diameter. The fiber diameter distribution were reported as first, second and third quartile as 25$^{th}$, 50$^{th}$ and 75$^{th}$ percentile. To observe cardiac cell morphology on fibrous scaffolds by SEM, after 4 days culturing the samples were fixed with 2% of glutaraldehyde/paraformaldehyde for 4 hours and dehydrated with a graded concentration (30-100%) ethanol. Then the samples were dried with a critical point dryer and sputter coated with Pt/Pd for 90 s before imaging.

D. Immunostaining: Cardiomyocytes were fixed 4 days after seeding. Media was removed, cells were rinsed in 37° C. PBS, then immediately fixed in a 4% solution of paraformaldehyde with 0.01% Triton X-100 in phosphate-buffered saline at 37° C. During the 15 minute fixation period, cells were equilibrated at room temperature. After fixation, myocytes were rinsed in room temperature PBS and stained. Myocytes were stained by inverting the coverslip on a solution of PBS containing 4',6'-diamidino-2-phenylindole hydrochloride (DAPI, 30 nM) (Invitrogen, Eugene, Oreg.). The first stain also contained a 1:100 dilution of anti-sarcomeric α-actinin monoclonal antibody (clone EA-53, Sigma, St. Louis, Mo.) and was incubated for 1 h at RT. Before the secondary stain, coverslips were rinsed in PBS. Secondary stains contained a 1:200 dilution of alexa-fluor 488 goat anti-mouse IgG (H+L) antibody (Invitrogen, Eugene, Oreg.). After incubation, coverslips were rinsed and mounted on glass coverslides until imaged.

E. Confocal Microscopy: Dispersion of fluorescent beads into the fibers was imaged with Zeiss LSM 5 LIVE Confocal Microscopy (Carl Zeiss, Dresden, Germany). Images were acquired under 40×/1.3 Oil DIC objective lens with 488 nm wavelength emission. Images of cardiomyocytes on PLA and gelatin fibers were acquired under 40×/1.3 Oil DIC objective lenses with 405 nm and 488 nm wavelength emissions. Images were analyzed and displayed using ImageJ (NIH, Bethesda, Md.).

F. Jet break-up analysis: To elucidate the mechanism of jet break-up and bead formation, the capillary number (Ca) was calculated for all samples based on definition of ratio of Weber number (We) to Reynolds number (Re). For calculating these two dimensionless numbers, jet exit velocity was estimated first in the rotating frame by measuring the difference in liquid height, Δh, and using the following formula:

$$V = \Delta h \cdot (D/2)^2 / R^2 \cdot t \quad (S2)$$

where R is radius of reservoir, D is diameter of the orifice, and t is the duration of experiments. Thereby, the jet exit velocity, U, based on the stationary frame was calculated as:

$$U = \sqrt{V^2 + R^2 \omega^2} \quad (S3)$$

where ω is the rotation speed in rad·s$^{-1}$.

Example 1

Rotary Spinning System: A Novel 3D Nanofiber Assembly Fabrication

In order to produce polymeric fibers, e.g., nano-scale fibers, a high speed rotating nozzle was exploited to form a polymer jet which undergoes extensive stretching before solidification (FIG. 2a). Termed rotary jet-spinning (RJS), the RJS system consisted of a reservoir with two side wall orifices that was attached to the shaft of a motor with controllable rotation speed. To facilitate the fiber collection a flexible air foil is placed on the shaft above the reservoir. The polymer solution was continuously fed to the reservoir at a rate sufficient to maintain a constant hydrostatic pressure and continuous flow. The resulting fibers were collected either on a stationary, surrounding cylindrical collector or on coverslips which were held against the collector wall. The fiber production process is composed of (i) jet-initiation to induce flow of the polymer solution through the orifice, (ii) jet-extension to increase surface area of the propelled polymer stream, and (iii) solvent evaporation to solidify and shrink the polymer jet. During the first step (FIG. 2b-i), a combination of hydrostatic pressure and centrifugal pressure at the far end of capillary (Ducree, J., et al. (2007) *Journal of Micromechanics and Microengineering* 17(7):S103-S115) exceeds the flow-resistant capillary forces and propels the polymer liquid through the nozzle capillary as a jet. The outward radial centrifugal force stretches the polymer jet as it is projected towards the collector wall (FIG. 2b-ii), but the jet travels in a curled trajectory due to rotation-dependent inertia. Stretching of the extruded polymer jet is critical in reducing jet diameter over the distance from the nozzle to the collector. Concurrently, the solvent in the polymer solution evaporates, solidifying and contracting the jet (FIG. 2b-iii). The solvent evaporation rate depends on its volatility. If the solvent is highly volatile, the jets form thicker fibers as the rapidly evaporating solvent potentiates rapid solidification, hindering the jet extension. The primary challenges in this process are optimizing the polymer solution properties (viscoelasticity and surface tension), solvent volatility, capillary diameter, and collector radius to not only produce ultra fine fibers but also prevent jet rupture and the formation of droplets due to Plateau-Rayleigh instability (Oliveira, M. S. N., et al. (2006) *Journal of Non-Newtonian Fluid Mechanics* 137(1-3):137-148). The jet break-up may be estimated by the capillary number, defined as the ratio of Weber number (We) to Reynolds number (Re), Ca=We/Re, which characterizes the ratio of the viscous force to the surface tension force (Oliveira, M. S. N., et al. (2006) *Journal of Non-Newtonian Fluid Mechanics* 137(1-3):137-148). Here We=$\rho U^2 D/\gamma$ and Re=$\rho UD/\eta$ where ρ, η and γ are density, dynamic viscosity and surface tension of polymer solution, respectively, U is the polymer jet exit speed based on a stationary frame (see Supporting Information for measurement of jet speed) and D is the orifice diameter. A lower capillary number results in shorter jet length and earlier jet break-up to isolated droplets (Oliveira, M. S. N., et al. (2006) *Journal of Non-Newtonian Fluid Mechanics* 137(1-3):137-148).

Example 2

Fabrication of Polymeric Fibers Using A Rotary Spinning System

Using a rotary spinning system described herein, 3-dimensional micron, submicron and nano-scale structures from a variety of synthetic and naturally occurring polymers. Polymeric fibers were produced from poly (lactic acid) (PLA) in chloroform (FIGS. 2c-2e), poly (ethylene oxide) in water (FIG. 2f), poly (acrylic acid) in water at different conductivities (neutralized with sodium hydroxide) (FIGS. 2g and 2h), gelatin in mild acetic acid (FIG. 2i), an emulsion of gelatin in PLA (FIG. 2j) and PEO doped with fluorescent spherical beads (FIG. 2k).

The successful production of polymeric fibers using a variety of synthetic and naturally occurring polymers, demonstrates that the devices methods described herein provide a rapid and facile technique of polymeric fiber, e.g., nanofiber fabrication without electrical propulsion which is capable of fabricating 3D aligned polymeric fibers, e.g., nanofiber, structures from a variety of polymers.

Example 3

Fabrication of Polymeric Fibers Using A Rotary Spinning System

Using a rotary spinning system described herein, 3-dimensional micron, submicron and nano-scale structures of biodegradable polylactic acid (PLA) polymer and hydrophilic polyethylene oxide (PEO) polymer were fabricated.

PLA was dissolved in either chloroform or dichloromethane and PEO was dissolved in either water, or a water/ethanol mixture. Various concentrations of solutions of the aforementioned polymers were prepared by mixing different weights of dry polymer in the corresponding solvents and then fed through a material feeding tube made of polyethylene into a rotating reservoir including two sidewall orifices. The resulting fibers were collected on the stationary collector. The spatial and hierarchical structure of the produced fibers was changed by altering rotation speed, polymer solution concentration, viscosity of polymer solution, polymer molecular weight, volatility of solvent, geometry of collector and reservoir. Table 1 describes the production variables and the features of the polymeric fibers fabricated uner the various production variables. As described in more detail below, continuous aligned PLA fibers with diameters ranging from 50-3500 nm were produced and by increasing the rotation speed from 4,000 to 12,000 rpm, the fiber diameter (median±median standard error) dropped from 1143±50 to 424±41 nm.

The effect of polymer concentration on the formation of polymeric fibers was also determined at 12,000 rpm rotation speed using polymer solutions of PLA in chloroform at 4%, 6%, 8% and 10% weight/volume in a rotary spinning system as described herein having two opposing sidewall orifices having a diameter of 100 micrometers. As depicted in the scanning electron micrographs shown in FIG. 4, a 4% solution of PLA resulted in the fabrication of beads; both 6% and 8% solutions of PLA resulted in the fabrication of continuous fibers, with the fibers fabricated using an 8% solution of PLA having a smaller diameter than the fibers fabricated using the 6% PLA solution; and a 10% PLA solution resulted in the fabrication of continuous fibers having a bimodal distribution of diameters.

Accordingly, at low polymer concentration only beads or beads-on-string structure were formed, but by increasing

TABLE 1

Composition and parameter values of all PLA solutions[a]

| Conc | Rotation | $\eta_0$ | $\gamma$ | $\rho$ | U | | | | Fiber | Fiber Diameter Parameters (nm) | | |
|---|---|---|---|---|---|---|---|---|---|---|---|---|
| wt % | Rpm | mPa·s | mN·m$^{-1}$ | g·cm$^{-3}$ | cm/s | We | Re | Ca | feature | Q1 | Q2 | Q3 |
| 10 | 12,000 | 282 | 27 | 1.54 | 398 | 150 | 3.8 | 40 | Continuous Fiber | 833 | 1630 | 2168 |
| 8 | 4,000 | 113 | 27 | 1.52 | 133 | 18 | 3.1 | 6 | Continuous Fiber | 782 | 1143 | 1740 |
| | 8,000 | | | | 266 | 68 | 6.1 | 11 | Continuous Fiber | 369 | 468 | 679 |
| | | | | | 399 | 153 | 9.2 | 17 | Continuous Fiber | 285 | 424 | 742 |
| 6 | 4,000 | 46 | 26 | 1.51 | 133 | 17 | 7.5 | 2.4 | Fiber + Many beads | 255 | 571 | 825 |
| | 12,000 | | | | 399 | 158 | 23 | 7 | Fiber + Few beads | 421 | 566 | 795 |
| 4 | 12,000 | 21 | 26 | 1.50 | 400 | 158 | 51 | 3 | Only Beads | N/A | N/A | N/A |
| 8* | 12,000 | 113 | 27 | 1.52 | 399 | 285 | 17 | 17 | Continuous Fiber | 612 | 962 | 1299 |

[a]Q1, Q2 and Q3 are first, second and third quartile of fiber diameter distribution which represent 25$^{th}$, 50$^{th}$ and 75$^{th}$ percentile, respectively. $\eta_0$, $\gamma$ and $\rho$ are shear viscosity, surface tension and density of the solution, U is the jet speed, We, Re and Ca are Weber number, Reynolds number and capillary number, respectively. Orifice geometry for all samples was D = 340 μm, L:D = 9 except for the (*) was D = 650 μm, L:D = 4.5. Fiber diameters can be tailored with the orifice diameters (see Supporting Information for more detail on orifice geometry). These data suggest that by decreasing the length to diameter ratio of the orifice, the pressure drop at the orifice decreases and the rate of solution outflow increases, resulting in larger diameter fibers.

A. The Effect of Polymer Concentration on the Fabrication of 3D Polymeric Fibers.

Figure 3A:
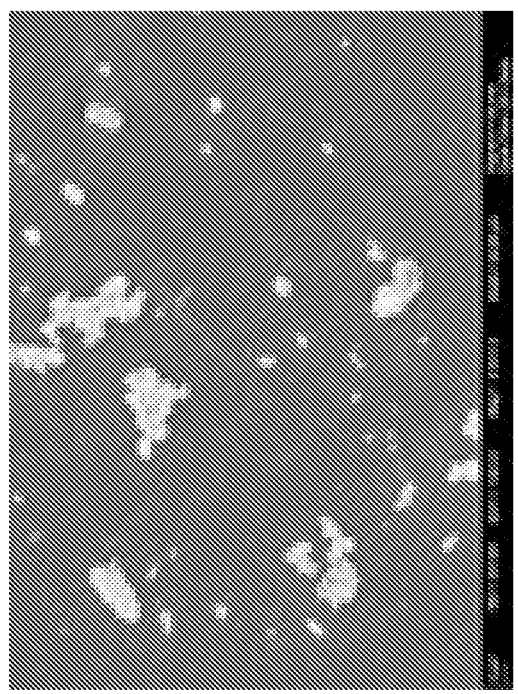
Figure 3B:
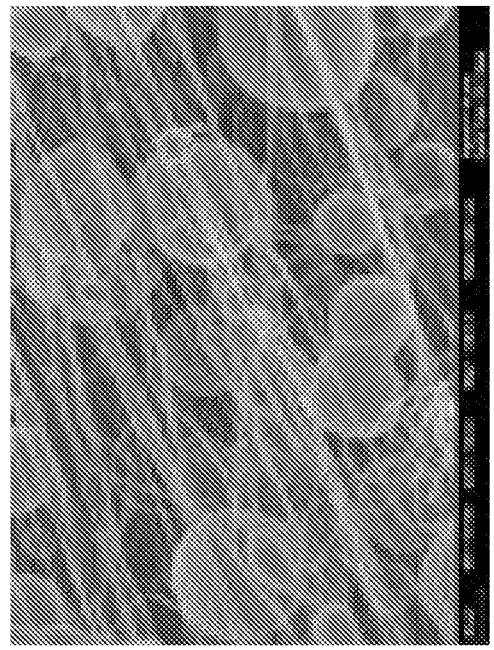
Figure 3B:
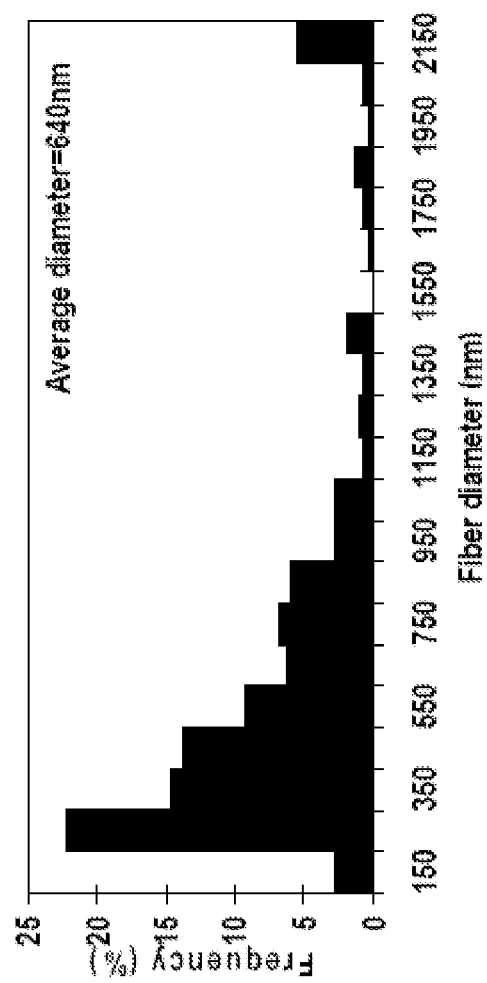
Figure 3D:
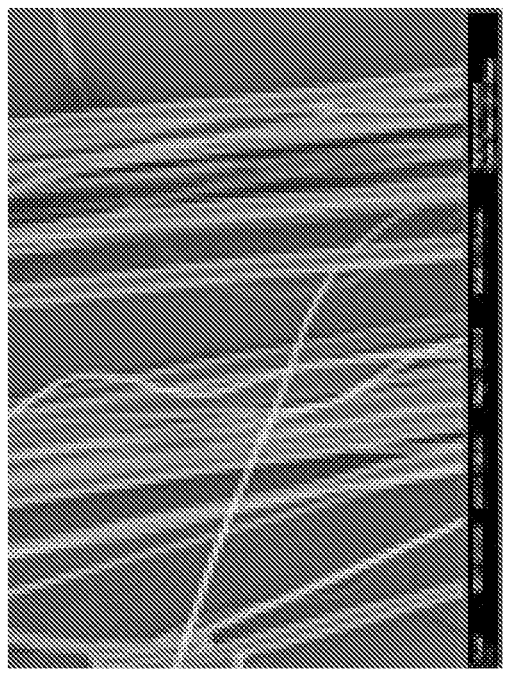
Figure 3C:
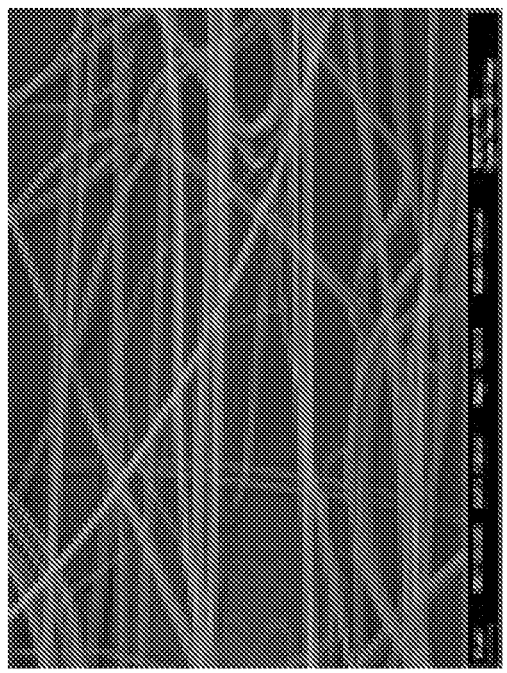
Figure 3C:
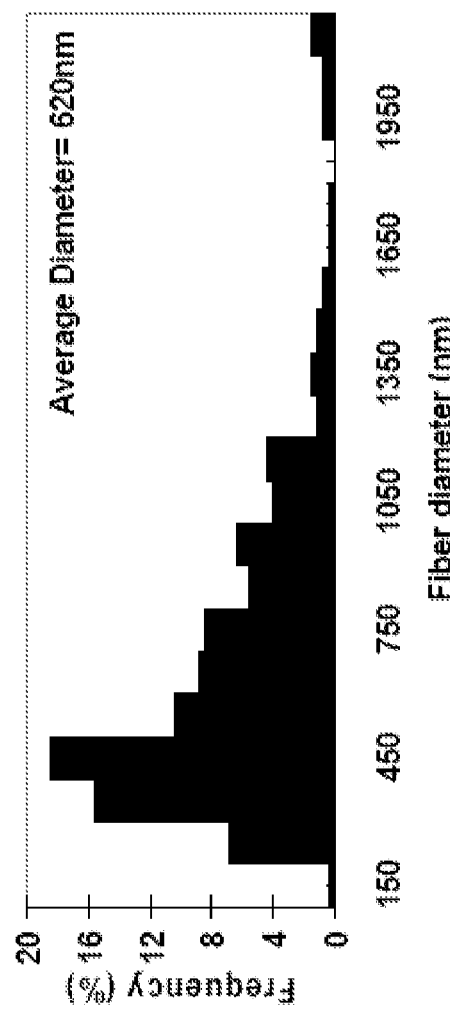
Figure 3D:
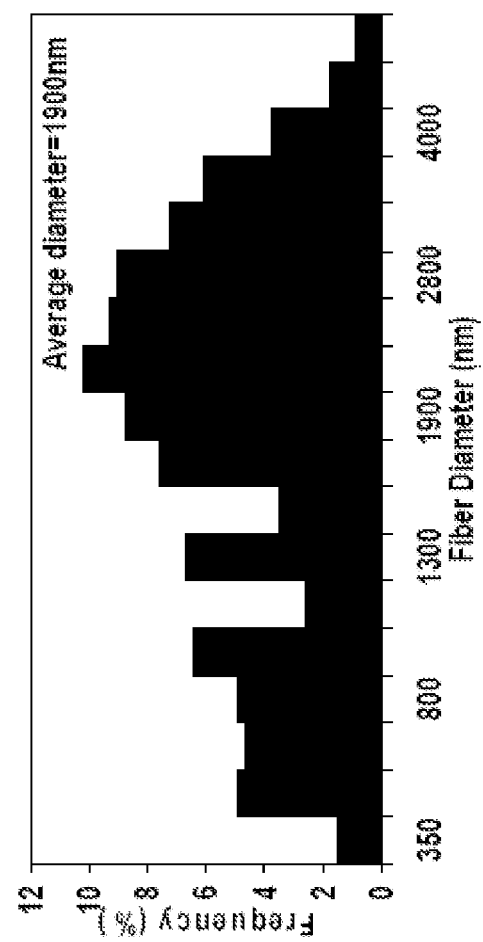

Using a 4% weight solution of polylactic acid (PLA) in chloroform at 10,000 rpm rotation speed, beads are formed due to insufficient polymer entanglement and Rayleigh instability driven by surface tension forces (FIG. 3A). Use of a 6% weight solution of polylactic acid (PLA) in chloroform at 10,000 rpm rotation speed resulted in the formation of beads-on-string due to insufficient polymer entanglement and Rayleigh instability driven by surface tension forces (FIG. 3B). FIG. 3B' shows the size distribution of the average diameter of the fibers formed in using a 6% weight solution of polylactic acid (PLA) in chloroform at 10,000 rpm rotation speed. Use of an 8% weight solution of polylactic acid (PLA) in chloroform at 10,000 rpm rotation speed resulted in the formation of continuous fibers (FIG. 3C). FIG. 3C' shows the size distribution of the average diameter of the fibers formed using a 6% weight solution of polylactic acid (PLA) in chloroform at 10,000 rpm rotation speed. Using a 10% weight solution of polylactic acid (PLA) in chloroform at 10,000 rpm rotation speed continuous fibers with a bimodal distribution of diameters are formed (FIG. 3D). FIG. 3D' shows the size distribution of the average diameter of the fibers formed using a 10% weight solution of polylactic acid (PLA) in chloroform at 10,000 rpm rotation speed.

polymer concentration to higher than 6% w/v, continuous fibers with less or no beads were formed.

B. The Effect of Rotation Speed on the Average Diameter, Diameter Distribution and Fiber Alignment on 3D Polymeric Fibers.

The effect of rotation speed was also determined using an 8% PLA in chloroform polymer solution. At 5,000 rpm rotation speed tangled continuous fibers with an average diameter of 557 nanometers were fabricated (FIGS. 5A and 5B). At 7,000 rpm rotation beads-on-string with an average diameter of 497 nanometers were fabricated (FIGS. 6A and 6B). At 10,000 rpm rotation continuous fibers with an average diameter of 440 nanometers were fabricated (FIGS. 7A and 7B).

FIG. 8 also depicts the effect of rotation speed on the fabrication of polymeric fibers using an 8% weight/volume solution of PLA in chloroform at 4,000, 8,000, and 12,000 rpm in a rotary spinning system as described herein having two opposing sidewall orifices having a diameter of 100 micrometers. The scanning electron micrographs show that at 4,000 rpm tangled, continuous fibers are produced having an average diameter of 1143 nanometers; at 8,000 rpm, continuous fibers are produced having an average diameter of 468 nanometer; and at 12,000 rpm, continuous fibers are produced having an average diameter of 424 nanometers. The graph in FIG. 8 shows the distribution of fiber diameters formed at various rotation speeds.

Accordingly, by increasing rotor speed average, the diameter of produced fibers can be decreased. In addition, alignment of fibers increased dramatically with increasing rotation speeds.

Without wishing to be bound by theory, the mechanism of RJS fiber formation is the optimization of the competing centrifugal forces and jet surface tension. The surface tension causes jet instability and bead formation (Lord, R. (1878) *Proceedings of the London Mathematical Society* s1-10(1): 4-13) while the centrifugal force accelerates a slender liquid stream where solvent evaporation and polymer chain elongation occur simultaneously. Thus, higher centrifugal force induces greater extension and thinning of the polymer jet which results in thinner fiber diameters. To test this hypothesis, the rotation speed was varied while maintaining a constant PLA solution concentration. The centrifugal force per solution volume increases significantly with rotation speed, while the surface tension remains the same (Table 1). The fiber diameter distribution (FIG. 8) is much wider at lower rotation speed and the probability of bead formation is higher. Next, the rotation speed was held constant while varying the polymer concentration in the solvent. Without wishing to be bound by theory, the surface tension of the polymer solution and its tendency to induce beading could be compensated for by varying the polymer concentration. When the rotation speed was held constant, at low polymer concentrations (4 wt %) RJS resulted in polymer beads. As the polymer concentration (c) (4 wt %<c<10 wt %) was increased, the increased polymer chain entanglement stabilized the jet resulting in fiber formation. This data demonstrates that fiber formation is a function of the polymer concentration where an optimal range of concentrations increases the likelihood of polymer chain entanglement (Shenoy, S. L., et al. (2005) *Polymer* 46(10):3372-3384), resisting beading and resulting in fine fibers. Beyond this optimal range (10 wt % and higher), the higher solution viscosity limits solvent evaporation and necking, resulting in thicker fibers.

An additional contributor to fiber formation is polymer chain entanglement density. As the polymer concentration increases, a deformable entangled network of polymer chains forms as a direct consequence of chain overlap. In low concentration (c) polymer solutions, lower than critical concentration value, $c^*$, ($c<<c^*$) chain overlapping is absent. As the polymer concentration is increased ($c \rightarrow c^*$), chain entanglement is still insufficient for formation of bead-free fibers (Shenoy, S. L., et al. (2005) *Polymer* 46(10):3372-3384; Wang, C., et al. (2009) *Polymer* 50(25):6100-6110). At solution concentrations above the critical concentration ($c>c^*$), sufficient chain entanglement produces uniform continuous fibers without beads. The specific viscosity of polymer solutions as a function of concentration was measured. As depicted in FIG. 9a, changes in the slope marked the onset of the semidilute unentangled, entangled and concentrated regimes, the latter ($c^*$) occurring at 6 wt % polymer solution concentration.

In order to determine how the capillary number ($Ca$) and polymer solution concentrations affect the quality of fiber production, bead-free fibers were used to define the highest production quality. The $Ca$ number represents the magnitude of the centrifugally-induced shearing forces relative to the surface tension (Eggers, J. (1997) *Reviews of Modern Physics* 69(3):865-929. An increased likelihood of continuous fibers at high $Ca$ numbers was observed (FIG. 9b). As expected, for $c<c^*$, RJS produced only beads, however, for $c>c^*$, chain entanglement was sufficient to potentiate fiber formation. At lower rotation speeds and Ca, fiber malformations were occasionally present (FIG. 9b), however, with higher Ca and rotation speeds, higher quality fiber production was achievable. These data demonstrate that by increasing the rotation speed, the polymer jet travels faster and stretches rapidly, enhancing solvent evaporation. Rapid solvent evaporation increases polymer concentration and solution viscosity, the latter due to chain entanglement. This stabilizes the jet and resists surface tension-induced bead formation.

Example 4

Fabrication of Tissue Engineered Scaffold Using Polymeric Fibers Fabricated Using A Rotary Spinning System To test the ability of a rotary spinning system described herein to produce tissue engineering scaffolds, anisotropic, fibrous constructs were prepared (FIG. 10a, 10b). Chemically dissociated neonatal rat ventricular myocytes were seeded on the constructs where they bound to, and spontaneously aligned with the fibers (FIG. 10c). Individual myocytes organized their contractile cytoskeleton with respect to the external cue provided by the extracellular fibers, as indicated by the alignment of the sarcomeric Z lines perpendicular to the fiber alignment (FIG. 10d). As depicted in the example in FIG. 10e, multicellular constructs self-organized with respect to the fibers, forming beating, anisotropic muscle with aligned and elongated myocytes and ordered myofibrils, as seen previously observed with other cardiac tissue engineering techniques (Feinberg, A. W., et al. (2007) *Science* 317 (5843):1366-1370; Alford, P. W. et al. (2010) *Biomaterials* 31(13):3613-3621. Accordingly, use of a rotary spinning system to fabricate polymeric fibersis a simple means of forming anisotropic scaffolds of biodegradable polymeric fibers made from synthetic and natural polymers.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by $\frac{1}{20}$th, $\frac{1}{10}$th, $\frac{1}{5}$th, $\frac{1}{3}$rd, $\frac{1}{2}$, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed:

1. A device for the fabrication of a submicron or nanometer dimension polymeric fiber, comprising
a rotary spinning system, said system comprising
a rotating reservoir suitable for accepting a polymer and comprising an orifice having a diameter of about 1 micrometer to about 400 micrometers, the orifice configured to form a submicron or nanometer dimension polymeric fiber by ejecting a jet of said polymer radially outward from the orifice during rotation of said reservoir at a rotational speed of about 24,000 rpm to about 50,000 rpm;
a motor for imparting rotational motion to the reservoir, the motor being configured to impart a rotational speed of about 24,000 rpm to about 50,000 rpm to the reservoir;
a collector for accepting said formed submicron or nanometer dimension polymeric fiber, at least a portion of the collector disposed directly radially outward from the rotating reservoir; and
a flexible air foil for facilitating collection of said radially ejected submicron or nanometer dimension polymeric fiber on the portion of the collector disposed directly radially outward from the rotating reservoir, the flexible air foil being attached to a shaft of the motor above the reservoir;
wherein the device is free of an electrical field.

2. The device of claim 1, wherein said reservoir comprises two orifices.

3. The device of claim 1, wherein said orifice has a diameter of about 50 micrometers to about 400 micrometers.

4. The device of claim 1, further comprising a component suitable for continuously feeding said polymer into said rotating reservoir.

5. The device of claim 1, wherein the reservoir further comprises a heating element.

6. The device of claim 2 wherein said orifices are of the same diameter.

7. The device of claim 2, wherein said orifices are of different diameters.

8. The device of claim 1, where the orifice is configured to form the submicron or nanometer dimension polymeric fiber by ejecting the jet of said polymer from the orifice under a combination of hydrostatic and centrifugal pressure that exceeds the flow-resistant capillary forces in the orifice during rotation of said reservoir at the rotational speed of about 24,000 rpm to about 50,000 rpm.

9. The device of claim 1, wherein the collector is a cylindrical collector.

10. A method for fabricating a submicron or nanometer dimension polymeric fiber, comprising
providing the device for the fabrication of a submicron or nanometer dimension polymeric fiber of claim 1;
continuously feeding a polymer into the rotating reservoir; and
rotating the rotary spinning system at a speed and for a time sufficient to form the submicron or nanometer dimension polymeric fiber.

11. The method of claim 10, wherein said rotary spinning system is rotated at a speed of about 24,000 to about 50,000 rpm.

12. The method of claim 10, wherein said rotary spinning system is rotated for a time of about 1 minute to about 100 minutes.

13. The method of claim 10, wherein said polymer is selected from the group consisting of poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyphosphazenes, polygermanes, and polyorthoesters, polyesters, polyamides, polyolefins, polycarbonates, polyaramides, polyimides.

14. The method of claim 10, wherein said polymer is a naturally occurring polymer selected from the group consisting of proteins, polysaccharides, lipids, nucleic acids or combinations thereof.

15. The method of claim 10, wherein said polymer is fed into said rotating reservoir as a polymer solution.

16. The method of claim 10, wherein a plurality of submicron or nanometer dimension polymeric fibers are formed.

17. The method of claim 16, wherein said plurality of submicron or nanometer dimension polymeric fibers are contacted with a plurality of living cells.

18. The method of claim 17, wherein said cells are cultured such that a living tissue is produced.

19. The method of claim 16, wherein said plurality of submicron or nanometer dimension polymeric fibers are contacted with a biologically active agent.

20. The method of claim 16, wherein said plurality of submicron or nanometer dimension polymeric fibers are treated with a pharmaceutically active agent.

* * * * *